(12) United States Patent
Kim et al.

(10) Patent No.: US 10,676,732 B2
(45) Date of Patent: Jun. 9, 2020

(54) METHOD FOR DEVELOPING LYSINE DECARBOXYLASE MUTANT AND APPLICATION THEREOF

(71) Applicant: Seoul National University R&DB Foundation, Gwanak-gu, Seoul (KR)

(72) Inventors: Byung Gee Kim, Seoul (KR); Eun Young Hong, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 15/746,580

(22) PCT Filed: Jun. 14, 2016

(86) PCT No.: PCT/KR2016/006281
§ 371 (c)(1),
(2) Date: Jan. 22, 2018

(87) PCT Pub. No.: WO2017/022944
PCT Pub. Date: Feb. 9, 2017

(65) Prior Publication Data
US 2018/0291362 A1    Oct. 11, 2018

(30) Foreign Application Priority Data
Aug. 6, 2015 (KR) .................. 10-2015-0111115

(51) Int. Cl.
*C12N 9/88* (2006.01)
*C12N 1/21* (2006.01)
*C12P 13/00* (2006.01)
*C12N 15/60* (2006.01)

(52) U.S. Cl.
CPC .............. *C12N 9/88* (2013.01); *C12P 13/001* (2013.01); *C12Y 401/01018* (2013.01)

(58) Field of Classification Search
None
See application file for complete search history.

(56) References Cited

U.S. PATENT DOCUMENTS

| | | | |
|---|---|---|---|
| 6,187,296 B1 | 2/2001 | Levine | |
| 8,986,698 B2* | 3/2015 | Arnason | ............ C07K 14/765 |
| | | | 424/178.1 |
| 9,115,362 B2 | 8/2015 | Lee et al. | |
| 2009/0155296 A1 | 6/2009 | Levine | |
| 2013/0071888 A1 | 3/2013 | Sawai et al. | |
| 2015/0132808 A1 | 5/2015 | Mochizuki et al. | |

OTHER PUBLICATIONS

Uniprot, Accession No. P0A9H4, 2014, www.uniprot.org.*
Guo et al., Protein tolerance to random amino acid change, Proc. Natl. Acad. Sci. USA, 2004, 101, 9205-10.*
Kikuchi et al., Characterization of a Second Lysine Decarboxylase Isolated from *Escherichia coli*, J. Bacteriol., 1997, 179, 4486-92.*
International Search Report for PCT/KR2016/006281, dated Sep. 20, 2016, 2 pages.

* cited by examiner

*Primary Examiner* — Robert B Mondesi
*Assistant Examiner* — Todd M Epstein
(74) *Attorney, Agent, or Firm* — Stinson LLP

(57) ABSTRACT

The present invention relates to a method for producing a lysine carboxylase mutant strain, characteristics of the mutant strain, a gene encoding the lysine decarboxylase mutant strain, and a method for producing cadaverine using the same. The present invention provides lysine decarboxylase derived from *E. coli* improved through a protein engineering variation. In addition, the lysine decarboxylase mutant strain of the present invention increases activity, pH stability, and thermal stability at the time of producing cadaverine, thereby reducing production costs, through increasing a yield and productivity.

9 Claims, 11 Drawing Sheets
Specification includes a Sequence Listing.

FIG. 2

| Enzyme | Relative specific activity (%) |
|---|---|
| WT (LdcI) | 100 |
| F14Y | 102.6 |
| L7M | 103 |
| N8G | 105 |
| L7M/N8G | 156.8 |
| L7M/N8G/F14Y | 124.4 |
| F14C/K44C | 98.8 |
| L7M/N8G/F14C/K44C | 156.7 |

FIG. 3

| Enzyme | Tm value (°C) |
|---|---|
| WT (Ldcl) | 64.2 |
| F14Y | 65.2 |
| L7M/N8G/F14Y | 66.9 |
| F14C/K44C | 74.8 |
| L7M/N8G/F14C/K44C | 74.2 |

FIG. 9

LdcI
MNVIAILNHMGVYPKEEPIRELHRALERLNFQIVYPNDRDDLLKLIENNARLCGVIFDWDKYNLELCEEISKMNENLPLYAFANTYSTLDVSLNDLRLQISFFEYALGAAEDIANKIKQTTDEYINTILPPLTK
ALFKYVREGKYTFCTPGHMGGTAFQKSPVGSLFYDFFGPNTMKSDISISVSELGSLLDHSGPHKEAEQYIARVFNADRSYMVTNGTSTANKIVGMYSAPAGSTILIDRNCHKSLTHLMMMSDVTPIYFRPTRNA
YGILGGIPQSEFQHATIAKRVRETPNATWPVHAVITNSTYDGLLYNTDFIRKTLDVKSIHFDSAWVPYTNFSPIYEGKCGMSGGRVEGKVIYETQSTHKLLAAFSQASMIHVKGDVNEETFNEAYMMHTTTSPH
YGIVASTETAAAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVARYLDEHGIVVEKTGPYNLLFL
FSIGIDKTKALSLLRALTDFKRAFDLNLRVKNMLPSLYREDPEFYENMRIQELAQNIHKLIVHHNLPDLMYRAFEVLPTMVMTPYAAFQKELHGMTEEVYLDEMVGRINANMILPYPPGVPLVMPGEMITEESR
PVLEFLQMLCEIGAHYPGFETDIHGAYRQADGRYTVKVLREESKK (a)
MNVIAILNHMGVYYKEEPIRELHRALERLNFQIVYPNDRDDLLKLIENNARLCGVIFDWDKYNLELCEEISKMNENLPLYAFANTYSTLDVSLNDLRLQISFF
EYALGAAEDIANKIKQTTDEYINTILPPLTKALFKYVREGKYTFCTPGHMGGTAFQKSPVGSLFYDFFGPNTMKSDISISVSELGSLLDHSGPHKEAEQYIAR
VFNADRSYMVTNGTSTANKIVGMYSAPAGSTILIDRNCHKSLTHLMMMSDVTPIYFRPTRNAYGILGGIPQSEFQHATIAKRVKETPNATWPVHAVITNSTYD
GLLYNTDFIKKTLDVKSIHFDSAWVPYTNFSPIYEGKCGMSGGRVEGKVIYETQSTHKLLAAFSQASMIHVKGDVNEETFNEAYMMHTTTSPHYGIVASTETA
AAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVA
KYLDEHGIVVEKTGPYNLLFLFSIGIDKTKALSLLRALTDFKRAFDLNLRVKNMLPSLYREDPEFYENMRIQELAQNIHKLIVHHNLPDLMYRAFEVLPTMVM
TPYAAFQKELHGMTEEVYLDEMVGRINANMILPYPPGVPLVMPGEMITEESRPVLEFLQMLCEIGAHYPGFETDIHGAYRQADGRYTVKVLKEESKK (b)
MNVIAIMNHMGVYFKEEPIRELHRALERLNFQIVYPNDRDDLLKLIENNARLCGVIFDWDKYNLELCEEISKMNENLPLYAFANTYSTLDVSLNDLRLQISFFEYALGAAEDIANKIKQTTDEYINTILPPLTK
ALFKYVREGKYTFCTPGHMGGTAFQKSPVGSLFYDFFGPNTMKSDISISVSELGSLLDHSGPHKEAEQYIARVFNADRSYMVTNGTSTANKIVGMYSAPAGSTILIDRNCHKSLTHLMMMSDVTPIYFRPTRNA
YGILGGIPQSEFQHATIAKRVKETPNATWPVHAVITNSTYDGLLYNTDFIKKTLDVKSIHFDSAWVPYTNFSPIYEGKCGMSGGRVEGKVIYETQSTHKLLAAFSQASMIHVKGDVNEETFNEAYMMHTTTSPH
YGIVASTETAAAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVARYLDEHGIVVEKTGPYNLLFL
FSIGIDKTKALSLLRALTDFKRAFDLNLRVKNMLPSLYREDPEFYENMRIQELAQNIHKLIVHHNLPDLMYRAFEVLPTMVMTPYAAFQKELHGMTEEVYLDEMVGRINANMILPYPPGVPLVMPGEMITEESR
PVLEFLQMLCEIGAHYPGFETDIHGAYRQADGRYTVKVLKEESKK (c)
MNVIAILGHMGVYFKEEPIRELHRALERLNFQIVYPNDRDDLLKLIENNARLCGVIFDWDKYNLELCEEISKMNENLPLYAFANTYSTLDVSLNDLRLQISFFEYALGAAEDIANKIKQTTDEYINTILPPLTK
ALFKYVREGKYTFCTPGHMGGTAFQKSPVGSLFYDFFGPNTMKSDISISVSELGSLLDHSGPHKEAEQYIARVFNADRSYMVTNGTSTANKIVGMYSAPAGSTILIDRNCHKSLTHLMMMSDVTPIYFRPTRNA
YGILGGIPQSEFQHATIAKRVKETPNATWPVHAVITNSTYDGLLYNTDFIKKTLDVKSIHFDSAWVPYTNFSPIYEGKCGMSGGRVEGKVIYETQSTHKLLAAFSQASMIHVKGDVNEETFNEAYMMHTTTSPH
YGIVASTETAAAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVARYLDEHGIVVEKTGPYNLLFL
FSIGIDKTKALSLLRALTDFKRAFDLNLRVKNMLPSLYREDPEFYENMRIQELAQNIHKLIVHHNLPDLMYRAFEVLPTMVMTPYAAFQKELHGMTEEVYLDEMVGRINANMILPYPPGVPLVMPGEMITEESR
PVLEFLQMLCEIGAHYPGFETDIHGAYRQADGRYTVKVLKEESKK (d)
MNVIAIMGHMGVYFKEEPIRELHRALERLNFQIVYPNDRDDLLKLIENNARLCGVIFDWDKYNLELCEEISKMNENLPLYAFANTYSTLDVSLNDLRLQISFFEYALGAAEDIANKIKQTTDEYINTILPPLTK
ALFKYVREGKYTFCTPGHMGGTAFQKSPVGSLFYDFFGPNTMKSDISISVSELGSLLDHSGPHKEAEQYIARVFNADRSYMVTNGTSTANKIVGMYSAPAGSTILIDRNCHKSLTHLMMMSDVTPIYFRPTRNA
YGILGGIPQSEFQHATIAKRVKETPNATWPVHAVITNSTYDGLLYNTDFIKKTLDVKSIHFDSAWVPYTNFSPIYEGKCGMSGGRVEGKVIYETQSTHKLLAAFSQASMIHVKGDVNEETFNEAYMMHTTTSPH
YGIVASTETAAAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVARYLDEHGIVVEKTGPYNLLFL
FSIGIDKTKALSLLRALTDFKRAFDLNLRVKNMLPSLYREDPEFYENMRIQELAQNIHKLIVHHNLPDLMYRAFEVLPTMVMTPYAAFQKELHGMTEEVYLDEMVGRINANMILPYPPGVPLVMPGEMITEESR
PVLEFLQMLCEIGAHYPGFETDIHGAYRQADGRYTVKVLKEESKK (e)
MNVIAIMGHMGVYYKEEPIRELHRALERLNFQIVYPNDRDDLLKLIENNARLCGVIFDWDKYNLELCEEISKMNENLPLYAFANTYSTLDVSLNDLRLQISFFEYALGAAEDIANKIKQTTDEYINTILPPLTK
ALFKYVREGKYTFCTPGHMGGTAFQKSPVGSLFYDFFGPNTMKSDISISVSELGSLLDHSGPHKEAEQYIARVFNADRSYMVTNGTSTANKIVGMYSAPAGSTILIDRNCHKSLTHLMMMSDVTPIYFRPTRNA
YGILGGIPQSEFQHATIAKRVKETPNATWPVHAVITNSTYDGLLYNTDFIKKTLDVKSIHFDSAWVPYTNFSPIYEGKCGMSGGRVEGKVIYETQSTHKLLAAFSQASMIHVKGDVNEETFNEAYMMHTTTSPH
YGIVASTETAAAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVARYLDEHGIVVEKTGPYNLLFL
FSIGIDKTKALSLLRALTDFKRAFDLNLRVKNMLPSLYREDPEFYENMRIQELAQNIHKLIVHHNLPDLMYRAFEVLPTMVMTPYAAFQKELHGMTEEVYLDEMVGRINANMILPYPPGVPLVMPGEMITEESR
PVLEFLQMLCEIGAHYPGFETDIHGAYRQADGRYTVKVLKEESKK (f)
MNVIAILNHMGVYCKEEPIRELHRALERLNFQIVYPNDRDDLLCLIENNARLCGVIFDWDKYNLELCEEISKMNENLPLYAFANTYSTLDVSLNDLRLQISFFEYALGAAEDIANKIKQTTDEYINTILPPLTK
ALFKYVREGKYTFCTPGHMGGTAFQKSPVGSLFYDFFGPNTMKSDISISVSELGSLLDHSGPHKEAEQYIARVFNADRSYMVTNGTSTANKIVGMYSAPAGSTILIDRNCHKSLTHLMMMSDVTPIYFRPTRNA
YGILGGIPQSEFQHATIAKRVKETPNATWPVHAVITNSTYDGLLYNTDFIKKTLDVKSIHFDSAWVPYTNFSPIYEGKCGMSGGRVEGKVIYETQSTHKLLAAFSQASMIHVKGDVNEETFNEAYMMHTTTSPH
YGIVASTETAAAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVARYLDEHGIVVEKTGPYNLLFL
FSIGIDKTKALSLLRALTDFKRAFDLNLRVKNMLPSLYREDPEFYENMRIQELAQNIHKLIVHHNLPDLMYRAFEVLPTMVMTPYAAFQKELHGMTEEVYLDEMVGRINANMILPYPPGVPLVMPGEMITEESR
PVLEFLQMLCEIGAHYPGFETDIHGAYRQADGRYTVKVLKEESKK (g)
MNVIAIMGHMGVYCKEEPIRELHRALERLNFQIVYPNDRDDLLCLIENNARLCGVIFDWDKYNLELCEEISKMNENLPLYAFANTYSTLDVSLNDLRLQISFFEYALGAAEDIANKIKQTTDEYINTILPPLTK
ALFKYVREGKYTFCTPGHMGGTAFQKSPVGSLFYDFFGPNTMKSDISISVSELGSLLDHSGPHKEAEQYIARVFNADRSYMVTNGTSTANKIVGMYSAPAGSTILIDRNCHKSLTHLMMMSDVTPIYFRPTRNA
YGILGGIPQSEFQHATIAKRVKETPNATWPVHAVITNSTYDGLLYNTDFIKKTLDVKSIHFDSAWVPYTNFSPIYEGKCGMSGGRVEGKVIYETQSTHKLLAAFSQASMIHVKGDVNEETFNEAYMMHTTTSPH
YGIVASTETAAAMMKGNAGKRLINGSIERAIKFRKEIKRLRTESDGWFFDVWQPDHIDTTECWPLRSDSTWHGFKNIDNEHMYLDPIKVTLLTPGMEKDGTMSDFGIPASIVARYLDEHGIVVEKTGPYNLLFL
FSIGIDKTKALSLLRALTDFKRAFDLNLRVKNMLPSLYREDPEFYENMRIQELAQNIHKLIVHHNLPDLMYRAFEVLPTMVMTPYAAFQKELHGMTEEVYLDEMVGRINANMILPYPPGVPLVMPGEMITEESR
PVLEFLQMLCEIGAHYPGFETDIHGAYRQADGRYTVKVLKEESKK

FIG. 10A

Figure 10A:
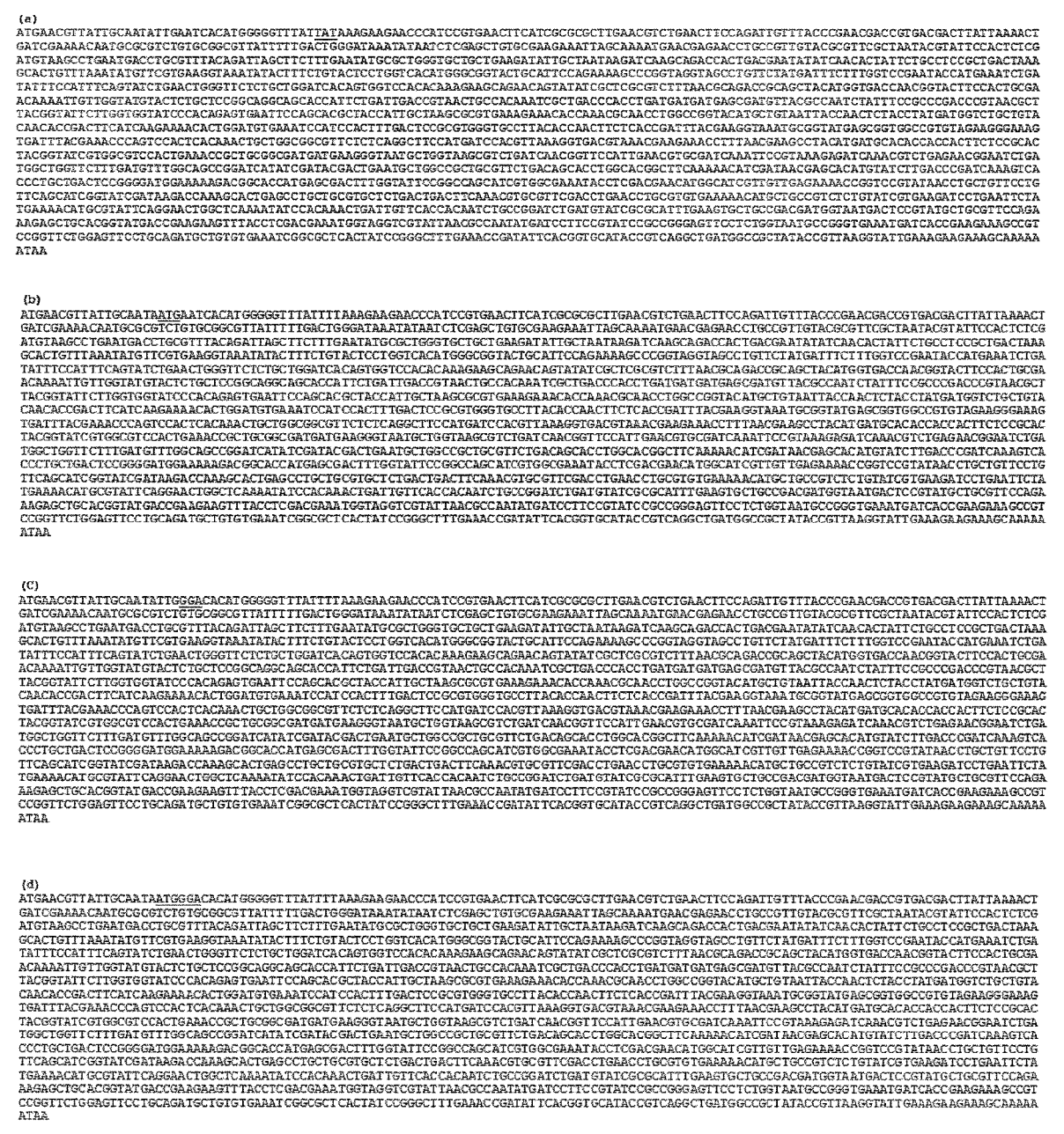

FIG. 10B (e)
```
ATGAACGTTATTGCAATAATGGGACACATGGGGGTTTATTATAAAGAAGAACCCATCCGTGAACTTCATCGCGCGCTTGAACGTCTGAACTTCCAGATTGTTTACCCGAACGACCGTGACGACTTATTAAAACT
GATCGAAAACAATGCGCGTCTGTGCGGCGTTATTTTTGACTGGGATAAATATAATCTCGAGCTGTGCGAAGAAATTAGCAAAATGAACGAGAACCTGCCGTTGTACGCGTTCGCTAATACGTATTCCACTCTCG
ATGTAAGCCTGAATGACCTGCGTTTACAGATTAGCTTCTTTGAATATGCGCTGGGTGCTGCTGAAGATATTGCTAATAAGATCAAGCAGACCACTGACGAATATATCAACACTATTCTGCCTCCGCTGACTAAA
GCACTGTTTAAATATGTTCGTGAAGGTAAATATACTTTCTGTACTCCTGGTCACATGGGCGGTACTGCATTCCAGAAAAGCCCGGTAGGTAGCCTGTTCTATGATTTCTTTGGTCCGAATACCATGAAATCTGA
TATTTCCATTTCAGTATCTGAACTGGGTTCTCTGCTGGATCACAGTGGTCCACACAAAGAAGCAGAACAGTATATCGCTCGCGTCTTTAACGCAGACCGCAGCTACATGGTGACCAACGGTACTTCCACTGCGA
ACAAAATTGTTGGTATGTACTCTGCTCCGGCAGGCAGCACCATTCTGATTGACCGTAACTGCCACAAATCGCTGACCCACCTGATGATGATGAGCGATGTTACGCCAATCTATTTCCGCCCGACCCGTAACGCT
TACGGTATTCTTGGTGGTATCCCACAGAGTGAATTCCAGCACGCTACCATTGCTAAGCGCGTGAAAGAAACACCAAACGCAACCTGGCCGGTACATGCTGTAATTACCAACTCTACCTATGATGGTCTGCTGTA
CAACACCGACTTCATCAAGAAAACACTGGATGTGAAATCCATCCACTTTGACTCCGCGTGGGTGCCTTACACCAACTTCTCACCGATTTACGAAGGTAAATGCGGTATGAGCGGTGGCCGTGTAGAAGGGAAAG
TGATTTACGAAACCCAGTCCACTCACAAACTGCTGGCGGCGTTCTCTCAGGCTTCCATGATCCACGTTAAAGGTGACGTAAACGAAGAAACCTTTAACGAAGCCTACATGATGCACACCACCACTTCTCCGCAC
TACGGTATCGTGGCGTCCACTGAAACCGCTGCGGCGATGATGAAGGGTAATGCTGGTAAGCGTCTGATCAACGGTTCCATTGAACGTGCGATCAAATCCGTAAAGAGATCAAACGTCTGAGAACGGAATCTGA
TGGCTGGTTCTTTGATGTTTGGCAGCCGGATCATATCGATACGACTGAATGCTGGCCGCTGCGTTCTGACAGCACCTGGCACGGCTTCAAAAACATCGATAACGAGCACATGTATCTTGACCCGATCAAAGTCA
CCCTGCTGACTCCGGGGATGGAAAAAGACGGCACCATGAGCGACTTTGGTATTCCGGCCAGCATCGTGGCGAAATACCTCGACGAACATGGCATCGTTGTTGAGAAAACCGGTCCGTATAACCTGCTGTTCCTG
TTCAGCATCGGTATCGATAAGACCAAAGCACTGAGCCTGCTGCGTGCTCTGACTGACTTCAAACGTGCGTTCGACCTGAACCTGCGTGTGAAAAACATGCTGCCGTCTCTGTATCGTGAAGATCCTGAATTCTA
TGAAAACATGCGTATTCAGGAACTGGCTCAAAATATCCACAAACTGATTGTTCACCACAATCTGCCGGATCTGATGTATCGCGCATTTGAAGTGCTGCCGACGATGGTAATGACTCCGTATGCTGCGTTCCAGA
AAGAGCTGCACGGTATGACCGAAGAAGTTTACCTCGACGAAATGGTAGGTCGTATTAACGCCAATATGATCCTTCCGTATCCGCCGGGAGTTCCTCTGGTAATGCCGGGTGAAATGATCACCGAAGAAAGCCGT
CCGGTTCTGGAGTTCCTGCAGATGCTGTGTGAAATCGGCGCTCACTATCCGGGCTTTGAAACCGATATTCACGGTGCATACCGTCAGGCTGATGGCCGCTATACCGTTAAGGTATTGAAAGAAGAAAGCAAAAA
ATAA
```

(f)
```
ATGAACGTTATTGCAATATTGAATCACATGGGGGTTTATTGTAAAGAAGAACCCATCCGTGAACTTCATCGCGCGCTTGAACGTCTGAACTTCCAGATTGTTTACCCGAACGACCGTGACGACTTATTATGTCT
GATCGAAAACAATGCGCGTCTGTGCGGCGTTATTTTTGACTGGGATAAATATAATCTCGAGCTGTGCGAAGAAATTAGCAAAATGAACGAGAACCTGCCGTTGTACGCGTTCGCTAATACGTATTCCACTCTCG
ATGTAAGCCTGAATGACCTGCGTTTACAGATTAGCTTCTTTGAATATGCGCTGGGTGCTGCTGAAGATATTGCTAATAAGATCAAGCAGACCACTGACGAATATATCAACACTATTCTGCCTCCGCTGACTAAA
GCACTGTTTAAATATGTTCGTGAAGGTAAATATACTTTCTGTACTCCTGGTCACATGGGCGGTACTGCATTCCAGAAAAGCCCGGTAGGTAGCCTGTTCTATGATTTCTTTGGTCCGAATACCATGAAATCTGA
TATTTCCATTTCAGTATCTGAACTGGGTTCTCTGCTGGATCACAGTGGTCCACACAAAGAAGCAGAACAGTATATCGCTCGCGTCTTTAACGCAGACCGCAGCTACATGGTGACCAACGGTACTTCCACTGCGA
ACAAAATTGTTGGTATGTACTCTGCTCCGGCAGGCAGCACCATTCTGATTGACCGTAACTGCCACAAATCGCTGACCCACCTGATGATGATGAGCGATGTTACGCCAATCTATTTCCGCCCGACCCGTAACGCT
TACGGTATTCTTGGTGGTATCCCACAGAGTGAATTCCAGCACGCTACCATTGCTAAGCGCGTGAAAGAAACACCAAACGCAACCTGGCCGGTACATGCTGTAATTACCAACTCTACCTATGATGGTCTGCTGTA
CAACACCGACTTCATCAAGAAAACACTGGATGTGAAATCCATCCACTTTGACTCCGCGTGGGTGCCTTACACCAACTTCTCACCGATTTACGAAGGTAAATGCGGTATGAGCGGTGGCCGTGTAGAAGGGAAAG
TGATTTACGAAACCCAGTCCACTCACAAACTGCTGGCGGCGTTCTCTCAGGCTTCCATGATCCACGTTAAAGGTGACGTAAACGAAGAAACCTTTAACGAAGCCTACATGATGCACACCACCACTTCTCCGCAC
TACGGTATCGTGGCGTCCACTGAAACCGCTGCGGCGATGATGAAGGGTAATGCTGGTAAGCGTCTGATCAACGGTTCCATTGAACGTGCGATCAAATCCGTAAAGAGATCAAACGTCTGAGAACGGAATCTGA
TGGCTGGTTCTTTGATGTTTGGCAGCCGGATCATATCGATACGACTGAATGCTGGCCGCTGCGTTCTGACAGCACCTGGCACGGCTTCAAAAACATCGATAACGAGCACATGTATCTTGACCCGATCAAAGTCA
CCCTGCTGACTCCGGGGATGGAAAAAGACGGCACCATGAGCGACTTTGGTATTCCGGCCAGCATCGTGGCGAAATACCTCGACGAACATGGCATCGTTGTTGAGAAAACCGGTCCGTATAACCTGCTGTTCCTG
TTCAGCATCGGTATCGATAAGACCAAAGCACTGAGCCTGCTGCGTGCTCTGACTGACTTCAAACGTGCGTTCGACCTGAACCTGCGTGTGAAAAACATGCTGCCGTCTCTGTATCGTGAAGATCCTGAATTCTA
TGAAAACATGCGTATTCAGGAACTGGCTCAAAATATCCACAAACTGATTGTTCACCACAATCTGCCGGATCTGATGTATCGCGCATTTGAAGTGCTGCCGACGATGGTAATGACTCCGTATGCTGCGTTCCAGA
AAGAGCTGCACGGTATGACCGAAGAAGTTTACCTCGACGAAATGGTAGGTCGTATTAACGCCAATATGATCCTTCCGTATCCGCCGGGAGTTCCTCTGGTAATGCCGGGTGAAATGATCACCGAAGAAAGCCGT
CCGGTTCTGGAGTTCCTGCAGATGCTGTGTGAAATCGGCGCTCACTATCCGGGCTTTGAAACCGATATTCACGGTGCATACCGTCAGGCTGATGGCCGCTATACCGTTAAGGTATTGAAAGAAGAAAGCAAAAA
ATAA
```

(g)
```
ATGAACGTTATTGCAATAATGGGACACATGGGGGTTTATTGTAAAGAAGAACCCATCCGTGAACTTCATCGCGCGCTTGAACGTCTGAACTTCCAGATTGTTTACCCGAACGACCGTGACGACTTATTATGTCT
GATCGAAAACAATGCGCGTCTGTGCGGCGTTATTTTTGACTGGGATAAATATAATCTCGAGCTGTGCGAAGAAATTAGCAAAATGAACGAGAACCTGCCGTTGTACGCGTTCGCTAATACGTATTCCACTCTCG
ATGTAAGCCTGAATGACCTGCGTTTACAGATTAGCTTCTTTGAATATGCGCTGGGTGCTGCTGAAGATATTGCTAATAAGATCAAGCAGACCACTGACGAATATATCAACACTATTCTGCCTCCGCTGACTAAA
GCACTGTTTAAATATGTTCGTGAAGGTAAATATACTTTCTGTACTCCTGGTCACATGGGCGGTACTGCATTCCAGAAAAGCCCGGTAGGTAGCCTGTTCTATGATTTCTTTGGTCCGAATACCATGAAATCTGA
TATTTCCATTTCAGTATCTGAACTGGGTTCTCTGCTGGATCACAGTGGTCCACACAAAGAAGCAGAACAGTATATCGCTCGCGTCTTTAACGCAGACCGCAGCTACATGGTGACCAACGGTACTTCCACTGCGA
ACAAAATTGTTGGTATGTACTCTGCTCCGGCAGGCAGCACCATTCTGATTGACCGTAACTGCCACAAATCGCTGACCCACCTGATGATGATGAGCGATGTTACGCCAATCTATTTCCGCCCGACCCGTAACGCT
TACGGTATTCTTGGTGGTATCCCACAGAGTGAATTCCAGCACGCTACCATTGCTAAGCGCGTGAAAGAAACACCAAACGCAACCTGGCCGGTACATGCTGTAATTACCAACTCTACCTATGATGGTCTGCTGTA
CAACACCGACTTCATCAAGAAAACACTGGATGTGAAATCCATCCACTTTGACTCCGCGTGGGTGCCTTACACCAACTTCTCACCGATTTACGAAGGTAAATGCGGTATGAGCGGTGGCCGTGTAGAAGGGAAAG
TGATTTACGAAACCCAGTCCACTCACAAACTGCTGGCGGCGTTCTCTCAGGCTTCCATGATCCACGTTAAAGGTGACGTAAACGAAGAAACCTTTAACGAAGCCTACATGATGCACACCACCACTTCTCCGCAC
TACGGTATCGTGGCGTCCACTGAAACCGCTGCGGCGATGATGAAGGGTAATGCTGGTAAGCGTCTGATCAACGGTTCCATTGAACGTGCGATCAAATCCGTAAAGAGATCAAACGTCTGAGAACGGAATCTGA
TGGCTGGTTCTTTGATGTTTGGCAGCCGGATCATATCGATACGACTGAATGCTGGCCGCTGCGTTCTGACAGCACCTGGCACGGCTTCAAAAACATCGATAACGAGCACATGTATCTTGACCCGATCAAAGTCA
CCCTGCTGACTCCGGGGATGGAAAAAGACGGCACCATGAGCGACTTTGGTATTCCGGCCAGCATCGTGGCGAAATACCTCGACGAACATGGCATCGTTGTTGAGAAAACCGGTCCGTATAACCTGCTGTTCCTG
TTCAGCATCGGTATCGATAAGACCAAAGCACTGAGCCTGCTGCGTGCTCTGACTGACTTCAAACGTGCGTTCGACCTGAACCTGCGTGTGAAAAACATGCTGCCGTCTCTGTATCGTGAAGATCCTGAATTCTA
TGAAAACATGCGTATTCAGGAACTGGCTCAAAATATCCACAAACTGATTGTTCACCACAATCTGCCGGATCTGATGTATCGCGCATTTGAAGTGCTGCCGACGATGGTAATGACTCCGTATGCTGCGTTCCAGA
AAGAGCTGCACGGTATGACCGAAGAAGTTTACCTCGACGAAATGGTAGGTCGTATTAACGCCAATATGATCCTTCCGTATCCGCCGGGAGTTCCTCTGGTAATGCCGGGTGAAATGATCACCGAAGAAAGCCGT
CCGGTTCTGGAGTTCCTGCAGATGCTGTGTGAAATCGGCGCTCACTATCCGGGCTTTGAAACCGATATTCACGGTGCATACCGTCAGGCTGATGGCCGCTATACCGTTAAGGTATTGAAAGAAGAAAGCAAAAA
ATAA
```

METHOD FOR DEVELOPING LYSINE DECARBOXYLASE MUTANT AND APPLICATION THEREOF

CROSS REFERENCE TO RELATED APPLICATIONS

This application is a U.S. national stage application of PCT Application No. PCT/KR2016/006281, filed Jun. 14, 2016 and claims priority to Korean application 10-2015-0111115, filed Aug. 6, 2015. Each of the above-cited applications is incorporated herein by reference in its entirety.

FIELD OF THE INVENTION

The present invention relates to a method for developing a mutant strain of lysine decarboxylase through protein engineering via enzyme mutagenesis, the analysis of the mutant strain produced, and biotransformation using the mutant strain enzyme.

BACKGROUND OF THE INVENTION

In the age of continuous depletion of the oil resources, recently studies on synthesizing a polymer precursor from biomaterial as opposed to oil resources lively continued. In particular, cadaverine (1,5-diaminopentane) having two amine groups at the two terminals and consisting of five carbon atoms, is a material for use as a polymer precursor, and moreover, for various application in the field of chemical industry. The examples include polyamides, polyurethanes, and chelating agents. As a part of the studies, a recent research on synthesizing cadaverine from lysine, or a research on producing cadaverine in mass from glucose or starch which are even cheaper than lysine, using biotransformation function of microorganism cells is actively in progress. As such, there may be various methods for producing cadaverine in mass using biotransformation technology via gene mutation of a host cell, but the starting material being starch or glucose, lysine synthesis can be performed via several steps of biotransformation procedures, and this lysine can be transformed to other compounds via various reactions. Because of this, lysine is used as a main starting material. One example of this is decarboxylation, and cadaverine can be synthesized by lysine decarboxylase reaction. The technology of producing lysine from glucose in microorganisms can already produce about 120 g/L from *Corynebacterium glutamicum*, and the mass production is commercialized in practice. Accordingly, a technology of transforming the highly concentrated lysine as a substrate to various compounds in a cell, or a technology of converting to cadaverine more efficiently in vitro by one-step reaction is necessary.

In the case of lysine decarboxylase, it is not present within *Corynebacterium glutamicum*, but it is known to be present in variously derived microorganisms. Among them in particular, lysine decarboxylase derived from *Escherichia coli* using PLP (pyridoxal-5'-phosphate) coenzyme is known to have high reactivity. In *Escherichia coli*, two types of lysine decarboxylase are present, LdcC lysine decarboxylase which is continuously expressed when the cell grows, and LdcI lysine decarboxylase which shows induced expressions only in condition of weak acidic pH are present. Houry research team of Toronto University of Canada, revealed the structure of LdcI lysine decarboxylase derived from *Escherichia coli*, and also revealed that the enzyme is in a form of a decamer consisting of 10 units. By the revealed structure of lysine decarboxylase and the mutation of amino acid residues, it became possible to predict what is the important element affecting the enzyme activity, and how the reaction mechanism works.

There are several disadvantages for using lysine decarboxylase LdcI derived from *Escherichia coli*, which is relatively high in activity, in a highly concentrated industrial reaction. Whilst it is high in activity in weak acidity (pH5.6), it has disadvantage of rapidly losing activity in neutrality or alkalinity. Because of this disadvantage, in order to perform repetitive reaction over long time with high concentration, increase in pH, thermostability and higher enzyme activity are required for LdcI enzyme. For these reasons, it is necessary to improve the enzyme reactivity throughout the overall pH through structural studies of the enzyme, and develop a mutant strain with increased stability for heat and pH, and thereby apply them to highly concentrated and continuous lysine biotransformation.

SUMMARY OF THE INVENTION

Features of the invention are defined in the appended claims. Other objects and features will be in part apparent and in part pointed out hereinafter.

BRIEF DESCRIPTION OF THE DRAWINGS

FIG. 2 shows relative specific activities of a single amino acid of a wild type (WT) lysine decarboxylase LdcI represented by SEQ ID NO: 15, and of the mutant strains thereof.

FIG. 3 shows the change in the single amino acid of lysine decarboxylase and the melting point temperature (Tm) of the protein of the combinatorial mutant strain thereof.

FIG. 9 shows the amino acid sequence of the mutant strain and wild type LdcI of lysine decarboxylase derived from *Escherichia coli* used in the present invention. Specifically, in FIG. 9, LdcI is an amino acid sequence of wild type LdcI (SEQ ID NO: 15), (a) is an amino acid sequence of F14Y (phenylalanine at position 14 is substituted with tyrosine in SEQ ID NO: 15) (SEQ ID NO: 1), (b) is an amino acid sequence of L7M (leucine at position 7 is substituted with methionine in SEQ ID NO: 15) (SEQ ID NO: 2), (c) is an amino acid sequence of N8G (asparagine at position 8 is substituted with glycine in SEQ ID NO: 15) (SEQ ID NO: 3), (d) is a combinatorial amino acid sequence of L7M (leucine at position 7 is substituted with methionine in SEQ ID NO: 15) and N8G (asparagine at position 8 is substituted with glycine) (SEQ ID NO: 4), (e) is a combinatorial amino acid sequence of L7M (leucine at position 7 is substituted with methionine in SEQ ID NO: 15), N8G (asparagine at position 8 is substituted with glycine in SEQ ID NO: 15) and F14Y (phenylalanine at position 14 is substituted with tyrosine in SEQ ID NO: 15) (SEQ ID NO: 5), (f) is a combinatorial amino acid sequence of F14C (phenylalanine at position 14 is substituted with cysteine in SEQ ID NO: 15) and K44C (lysine at position 44 is substituted with cysteine in SEQ ID NO: 15) (SEQ ID NO: 6), (g) is a combinatorial amino acid sequence of L7M (leucine at position 7 is substituted with methionine in SEQ ID NO: 15), N8G (asparagine at position 8 is substituted with glycine in SEQ ID NO: 15) and F14C (phenylalanine at position 14 is substituted with cysteine in SEQ ID NO: 15) and K44C (lysine at position 44 is substituted with cysteine in SEQ ID NO: 15) (SEQ ID NO: 7).

FIGS. 10A and 10B provide DNA sequences encoding the amino acid sequences of SEQ ID NOS: 1 to 7. Specifically, in FIGS. 10A and 10B, (a) is a DNA sequence encoding the amino acid of SEQ ID NO: 1 (SEQ ID NO: 8), (b) is a DNA sequence encoding the amino acid of SEQ ID NO: 2 (SEQ ID NO: 9), (c) is a DNA sequence encoding the amino acid of SEQ ID NO: 3 (SEQ ID NO: 10), (d) is a DNA sequence encoding the amino acid of SEQ ID NO: 4 (SEQ ID NO: 11), (e) is a DNA sequence encoding the amino acid of SEQ ID NO: 5 (SEQ ID NO: 12), (f) is a DNA sequence encoding the amino acid of SEQ ID NO: 6 (SEQ ID NO: 13), (g) is a DNA sequence encoding the amino acid of SEQ ID NO: 7 (SEQ ID NO: 14).

DETAILED DESCRIPTION OF THE INVENTION

Technical Task

Figure 1:
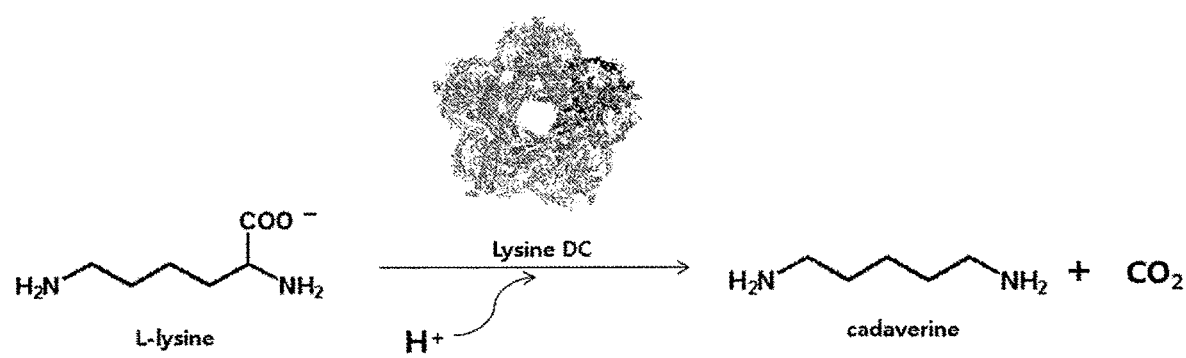
FIG. 1 is a schematic view showing a process of synthesizing cadaverine using lysine decarboxylase enzyme with L-lysine as a substrate according to the present invention.

In the conventional art, as to the production of cadaverine from lysine, most of the cases use LdcI lysine decarboxylase derived from *Escherichia Coli* which is highly active and is capable of overexpression in *Escherichia Coli*. Moreover, studies continued on use, etc. of LdcC together with LdcI on production of cadaverin by expressing them together, although the activity is low.

In previous patents and studies, the expression of the enzyme was controlled within the host cell in order to increase cadaverine production, or in order to easily discharge lysine and cadaverine outside the cell, methods such as overexpressing antiporters or blocking the dissolution route of cadaverine, was used, and thereby changing the other parts of the production route other than the enzyme, developed an indirect gene mutation to maximize cadaverine production from lysine. These studies can be very useful in lysine biotransformation using a cell, but it has its limits for use in biotransformation outside a cell, in vitro or in a reactor. As such, in order to use in biotransformation outside a cell, in vitro or in a reactor, it is more efficient to directly increase stability and enzyme activity of lysine decarboxylase. For this, studies continued to understand the mechanism of the reaction and to pursue remarkable increase in activity through mutation of the residues that are important for activity. However, to this moment, no study has ever reported that direct mutation is given to the lysine decarboxylase itself, overcoming the disadvantages in structure and stability of LdcI and LdcC enzyme of *Escherichia Coli*, and increasing the activity to use them in highly concentrated and long-time continuous reaction, etc.

In biotransformation from lysine to cadaverine, the first thing to consider is the pH of the reaction. In the mechanism of the reaction, because the carboxyl group of lysine runs out and the hydrogen ion of the reaction solution is used up, the pH of the reaction solution turns more alkali as the reaction develops. Accordingly, if the enzyme is sensitive to the pH, more activity is lost, and in order to achieve highly concentrated long-time reaction, the enzyme activity must be maintained throughout broad pH region.

In the case of lysine decarboxylase derived from *Escherichia coli*, the two enzymes that are LdcC and LdcI, are reported; however, the features of the two are different. In the case of LdcC, compared to LdcI, it has relatively low activity and expression as an enzyme which is always expressed when the cell grows, but maintains the activity throughout wide pH region overall. However, in the case of LdcI, it demonstrates high activity near pH 5.6, and when the reaction solution has pH 7.0, the activity rapidly decreases and remarkable decrease in activity is observed in alkali condition. Of course, LdcI is an enzyme which has higher inactivity over LdcC and thus it has advantages in highly concentrated reactions, but for LdcI to continue industrial highly concentrated and long-time continuous use reaction, pH stability, thermal stability, and higher enzyme activity are required.

Technical Solution

The present invention provides a method for producing the mutant strain through protein engineering mutagenesis of lysine decaroboxylase, and the gene sequence information searching the produced mutant strains and encoding the mutant strains.

The present invention also provides a method for analyzing the characteristics of the mutant strains and for producing cadaverine using them. That is, the present invention uses lysine decarboxylase derived from *Escherichia coli* improved by protein engineering mutagenesis and applies this to cadaverine production reaction.

The present invention also provides a method for logical prediction to produce lysine decarboxylase mutant strain, and thereby selects the part being the object of the protein and using the sequence, structure and function of the protein and a computer program, selects the residues of specific amino acid to perform mutagenesis.

The present invention also provides lysine decarboxylase gene comprising a sequence wherein the amino acid residues of lysine decarboxylase have transformed, and recombinant DNA vectors comprising thereof, and a host cell transformed to a recombinant DNA vector.

Advantageous Effects

The present invention increases the production efficiency and productivity of cadaverine through use of mutant strain of lysine decarboxylase with improved catalytic function, and thereby can reduce the production costs.

Moreover, increasing the enzyme pH stability in pH4 to 10, and increasing the enzyme thermal stability at the temperature in the range of 20° C. to 70° C., the present invention can increase the reusability of lysine decarboxylase and reduce the enzyme production costs as to the mass production of cadaverine.

Moreover, through the mass production of cadaverine, various use in homopolymer precursor, food and chemical additives, etc. can be made available, and the method for producing mutant strains of the present invention is applicable to other decarboxylase, in particular, decarboxylase using PLP coenzyme.

MODE FOR INVENTION

Terms that are used in the present invention are those that are generally used in the art, and the meaning thereof can be easily understood by any person skilled in the art. The definitions of the terms used herein will now be described in brief.

(1) "Lysine decarboxylase" means an enzyme that removes carboxy group from lysine.

(2) "PLP (pyridoxal-5'-phosphate)" added to lysine decarboxylase reaction is a coenzyme of an enzyme essentially used in a reaction.

(3) "Cell extract" means an extract of a microorganism including fucosyltransferase expressed therein.

(4) "Whole cell reaction" means a reaction that uses a cellular content obtained by lysis of a cell containing a certain enzyme, or a whole cell from which an enzyme had not been separated.

(5) "Hydrophilic amino acid" means an amino acid containing in its functional group a high-electronegativity element (oxygen, nitrogen or sulfur) capable of forming a hydrogen bond with water. Examples of the hydrophilic amino acid include serine, threonine, cysteine, tyrosine, aspartic acid, glutamic acid, asparagine, glutamine, histidine, lysine and arginine.

(6) "Hydrophobic amino acid" means an amino acid whose side chain is hydrophobic (i.e., has little or no affinity for a water molecule) and whose surface is insoluble in water. Examples of the hydrophobic amino acid include isoleucine, leucine, valine, methionine, phenylalanine, tryptophane, proline, glycine, and alanine.

(7) "PCR" refers to polymerase chain reaction and means a method for specifically amplifying any region of DNA.

(8) "Site directed mutagenesis" means introducing a particular mutation into a particular position of the nucleotide sequence of a gene.

(9) "Saturation mutagenesis" means introducing various mutations into a particular position of the nucleotide sequence of a gene. Specifically, "saturation mutagenesis" means inserting an NNK codon in place of the sequence to be mutated, into primers having complementary sequences, which bind to template strands, thereby inserting mutations through PCR. Here, N in the NNN or NNK codon represents a nucleotide selected from among A, T, G and C, and K represents a nucleotide selected from among T and G.

(10) "Vector" means a polynucleotide composed of single-stranded, double-stranded, circular or supercoiled DNA or RNA, and may include elements operatively linked at appropriate distances so as to be able to produce a recombinant protein.

Such elements may include a replication origin, a promoter, an enhancer, a 5' mRNA leader sequence, a ribosomal binding site, a nucleic acid cassette, termination and polyadenylation sites, and selectable marker sequences, and one or more of these elements may be omitted in specific applications. The nucleic acid cassette can include a restriction enzyme site for insertion of the nucleic acid sequence to be expressed. In a functional vector, the nucleic acid cassette contains the nucleic acid sequence to be expressed including translation initiation and termination sites. If necessary, a vector into which two kinds of cassettes can be inserted may also be used. The above-mentioned functions may additionally be sequenced.

A gene that is inserted into a recombinant DNA vector may be E. coli strain BW25113 (DE3) or BL21 (DE3) for expression, etc., but may vary depending on the kind of vector into which the gene is inserted. This vector and expression strain can be easily selected by any person skilled in the art.

(11) "Disulfide bond" is a shared bond between sulfur elements in a form —S—S— wherein two SH groups are producing in oxidation.

(12) "Reducing and non-reducing SDS PAGE (sodium dodecyl sulfate polyacrylamide gel electrophoresis)" means the comparison of the sizes of the protein when reducing is applied and not applied to a protein. This can confirm whether a shared bond is formed between sulfur elements in a form —S—S— wherein two SH groups are producing in oxidation.

(13) "pH indicator" refers to one that is mainly used to determine the neutralization point of titration or to determine the concentration of hydrogen ion (pH). The indicator is divided, according to hydrogen ion index, into an acid form and a base form, which have different colors, and this region is called "discoloration region". The concentration of hydrogen ion based on absorbance can be measured by spectrophotometry.

(14) "Specific activity" means the activity per unit amount of a pure protein from which impurities and other proteins were removed by enzyme purification. The specific activity is expressed as the number of units per mg protein. Here, one unit is the amount of enzyme that catalyzes the conversion of 1 μmol of a substrate per minute.

(15) "Relative specific activity" means a relative comparative value of the specific activity.

(16) "Melting point temperature of protein (TM)" represents the thermal stability of the protein, and means the temperature which the structure of the protein breaks.

(17) "Sequence alignment" means arranging the sequence of protein using a computer string sorting algorithm based on dynamic programming.

(18) "Sequence with different homology" means the part wherein the sequences are not consistent when the sequences are sorted for comparison of two proteins with different sequences.

The present invention provides a lysine decarboxylase mutant represented by any one sequence of base sequences below:

an amino acid sequence of SEQ ID NO: 1, wherein phenylalanine which is the amino acid at position 14 is substituted with tyrosine (F14Y), in the amino acid sequence of SEQ ID NO: 15 (LdcI);

an amino acid sequence of SEQ ID NO: 4, wherein leucine which is the amino acid at position 7 is substituted with methionine, and asparagine which is the amino acid at position 8 is substituted with glycine (L7M/N8G), in the amino acid sequence of SEQ ID NO: 15 (LdcI);

an amino acid sequence of SEQ ID NO: 5, wherein leucine which is the amino acid at position 7 is substituted with methionine, asparagine which is the amino acid at position 8 is substituted with glycine, and phenylalanine which is the amino acid at position 14 is substituted with tyrosine (L7M/N8G/F14Y), in the amino acid sequence of SEQ ID NO: 15 (LdcI);

an amino acid sequence of SEQ ID NO: 6, wherein phenylalanine which is the amino acid at position 14 is substituted with cysteine, and lysine which is the amino acid at position 44 is substituted with cysteine (F14C/K44C), in the amino acid sequence of SEQ ID NO: 15 (LdcI);

an amino acid sequence of SEQ ID NO: 7, wherein leucine which is the amino acid at position 7 is substituted with methionine, asparagine which is the amino acid at position 8 is substituted with glycine, phenylalanine which is the amino acid at position 14 is substituted with cysteine, and lysine which is the amino acid at position 44 is substituted with cysteine (L7M/N8G/F14C/K44C), in the amino acid sequence of SEQ ID NO: 15 (LdcI).

The amino acid sequence can have a homology of 90% or more in the range not adversely affecting the activity of lysine decarboxylase, preferably 95% or more of homology, more preferably 99% or more of homology.

The present invention provides a DNA encoding the lysine decarboxylase mutant.

The DNA can be used without limit provided that the DNA encodes the amino acid provided by the present invention, and comprises the sequence obtained by optimizing the DNA, and the DNA preferably can be the DNA sequence represented by any one sequence of SEQ ID NOS: 8 and 11 to 14.

The DNA sequence of SEQ ID NO: 8 is a sequence encoding the amino acid of SEQ ID NO: 1, the DNA sequence of SEQ ID NO: 11 is a sequence encoding the amino acid of SEQ ID NO: 4, the DNA sequence of SEQ ID NO: 12 is a sequence encoding the amino acid of SEQ ID NO: 5, the DNA sequence of SEQ ID NO: 13 is a sequence encoding the amino acid of SEQ ID NO: 6, the DNA sequence of SEQ ID NO: 14 is a sequence encoding the amino acid of SEQ ID NO: 7.

The present invention provides a recombinant DNA vector comprising the DNA, a host cell transformed with the recombinant DNA vector, and an extract of a host cell.

The vector and the host cell can be used without limit provided that a skilled person in the art can easily select.

Lysine decarboxylase of the present invention has increased pH stability at pH4 to 10, in particular, has remarkably increased pH stability at pH 4.4 to 8.5.

Moreover, lysine decarboxylase of the present invention has increased stability at a temperature in the range of 20° C. to 70° C., in particular, has increased stability at a temperature in the range of 35° C. to 70° C.

The present invention provides a method for producing cadaverine using any one selected from the group consisting of a host cell transformed with the recombinant DNA vector and an extract of the host cell, as a biocatalyst.

The method for producing can produce cadaverine from starch, glucose or lysine, preferably from glucose or lysine. Where cadaverine is produced from starch or glucose, lysine synthesis can be performed via several steps of biotransformation procedures, and decarboxylation can be performed on this synthesized lysine to produce cadaverine. The method for synthesizing lysine from starch or glucose can be used without limit provided that a skilled person in the art can easily select.

Moreover, the method for producing can produce cadaverine with highly concentrated lysine as a substrate. The preferable concentration of lysine is 1M to 6M, more preferably 1M to 3M.

The present invention provides a method for preparing a lysine decarboxylase mutant strain singularly or combinatorically substituting the residue of the amino acid at positions 7, 8, 14 or 44 of SEQ ID NO: 15 (LdcI).

The present invention provides a method for preparing a lysine decarboxylase mutant strain combinatorically substituting the sequence of the residue in order to make disulfide bond in the interface of the decamer of SEQ ID NO: 15 (LdcI).

In the interface of the decamer, the interface means the surfaces that are in contact when 10 proteins gather to form a decamer.

The present invention provides a method for producing a lysine decarboxylase mutant strain singularly or combinatorically substituting the residue positioned in the interface 8 Å of the decamer of SEQ ID NO: 15 (LdcI).

The method for producing a lysine decaraboxylase mutant strain specifically means the method for mutating the functional residues to perform a saturation mutagenesis or disulfide bonding through multiple sequences among the residues selected in the range of 4 to 6 Å from SEQ ID NOS: 7 to 50 which is the decamer interface part of the crystal structure of lysine decarboxylase.

In the present invention, the performance of saturated mutagenesis for functional residues of lysine decarboxylase can be done by performing saturated mutagenesis through PCR using NNK codon for the selected functional residues of lysine decarboxylase, or site directed mutagenesis through PCR using cysteine codon for disulfide bonding.

In the present invention, the search on the mutant strain of lysine decarboxylase can be done by performing screening by a colorimetric method using a pH indicator for the mutant strain libraries. Primary screening may proceed through a whole cell reaction, and specifically, after preparing a paper with the indicator on, attaching various mutant strain library cells to the paper with the indicator on, mutant strains which are similar in color in comparison with the wild type or which are changing more quickly in color can be visually selected. Preferably, for more accurate mutant strain search, secondary screening can be performed, and the secondary screening can distinguish using the spectrum absorbance the mutant strains showing quicker change in absorbance comparing the initial reaction speed with that of the wild type using the cell extract, after culturing by increasing the culture volume for the mutant strains selected in the primary screening.

EXAMPLES

The specific method of the present invention will be described in further detail with reference to the Examples, but the scope of the invention is not in any way limited to such Examples.

Analyzing Method for Enzyme Activity Using pH Indicator

The measurement of the activity of lysine decarboxylase by a colorimetric method is a method of measuring the change in pH when hydrogen bonds to the position where carboxy group of lysine is detached, and is proportional to the productivity of cadaverine.

The present invention selected pH indicator for use by optimal active pH of lysine decarboxylase. The enzyme activity analysis was carried out by mixing 4 mM of lysine, 0.2 mM PLP and 0.02 mM of pH indicator in 5 mM citric acid (Sodium-Citrate) buffer solution, in total of 200 uL by volume, in a 96-well plate. The reaction was carried out for 30 minutes, and in the case of Cresol purple, the increase in absorbance in 590 nm changing to purple was analyzed using a spectrum device with intervals of 30 seconds. The concentration of the generated hydrogen ion was calculated by the calibration curve according to the concentration of sodium hydroxide (NaOH). The enzyme reaction used the enzyme being 10% of the total reaction volume, and started by placing the substrate mixture in the enzyme. The enzyme activity (unit) was defined as the amount of the enzyme necessary for using up 1 umole of hydrogen generated per minute of decarboxylation at a room temperature.

Screening of Mutant Strain by Saturation Mutagenesis and Colorimetric Method

Using primers introduced with an NNK sequence (N=A, C, G or T, and K=G or T) resulting from substitution of the amino acid at position 14 of lysine decarboxylase with an amino acid at random, vectors were amplified by PCR to construct a library. The lysine decarboxylase of the present invention has methionine at position 1 when numbered from the first methionine. Each of the amplified lysine decarboxylase genes comprising the vector sequence was treated with Dpn I enzyme to remove the original plasmid, and then transformed into *E. coli* DH5 α. Mutated genes were extracted from all the generated colonies and transformed into *E. coli* BL21 (DE3). Each of the transformed colonies were inoculated into 500 μL of kanamycin-containing LB medium in a 96-well plate and shake-cultured at a temperature of 30 to 37° C. for 18-24 hours. Then, a portion of the culture was inoculated into 400 μL of a fresh LB containing 100 μg mL$^{-1}$ of kanamycin and IPTG (isopropyl β-D-a-thiogalactpyranoside), followed by culture at a temperature of 18 r for 20 hours. The cultured cells were centrifuged, and the cell pellets were resuspended in 10 mM Tris buffer solution 10000 uL, and the whole cell was used in a mutant strain screening reaction. Specifically, the whole cell comprising lysine decarboxylase was added to 180 μL of a reaction solution containing 4 mM lysine, 0.2 mM PLP, and 0.02 mM pH indicator, and 5 mM citric acid (Sodium-Citrate) buffer solution, and the mixture was allowed to react. The absorbance of the reaction mixture was measured at intervals of 30 seconds for change in 30 minutes.

Example 1: Specific Activity Measurement for the Mutant Strains of Lysine Decarboxylase The relative specific activities of the substitution mutant strain of lysine decarboxylase were analyzed using the same amount of protein for each via the enzyme activity analyzing method using the abovementioned pH indicator, and the reaction was performed at pH 5.6 and 37° C., to observe the reaction for 30 minutes. The results are shown in FIG. 2.

As shown in FIG. 2, most of the mutant strains have higher activity than the wile type, but among the mutant strains of F14, the mutant strain wherein the amino acid was substituted with tyrosine shows similar activity to the wild type strain. In the case of lysine decarboxylase LdcI, phenylalanine of F14 is positioned at alpha-helix of the interface, and the interface with both F14 and K44 switched with cysteine formed a disulfide bond and shows similar activity to the wild type strain. The mutant strain of L7 and N8 shows similar activity to the wild type strain when performing a singular mutagenesis, but in the case of L7M/N8G mutant strain, the activity increased by 56.8%. In the case of L7M/N8G/F14Y mutant strain, the activity increased by 24.4%, and L7M/N8G/F14C/K44C mutant strain, the activity increased by 56.7%.

Example 2: Melting Point (Tm Value) Measurement of the Mutant Strains of Lysine Decarboxylase In order to observe the thermal stability of the combinatorial mutant strain or the change of the singular amino acid and a wild type strain of lysine decarboxylase which completed protein refining, the melting point temperature (Tm) of the protein was observed. As the temperature was gradually increased from 0° C. to 100° C., the melting point temperature which the structure of the protein breaks was observed, and the melting point was observed as a change in fluorescence by placing sypro orange in 1 mg of protein. The change in temperature was gradually made from 30 minutes to 1 hour, and the analysis was carried out by the analyzing method in accordance with the sypro orange fluorescence change specified above. The results were shown in FIG. 3.

As shown in FIG. 3, it was found that F14C/K44C can absorb relatively various mutant strains, and in the case of F14C/K44C and L7M/N8G/F14C/K44C mutant strains, it was found that the Tm value increased by 10.6° C. and 10.0° C. respectively compared to the wild type.

Example 3: pH Stability Measurement of Lysine Decarboxylase Mutant Strain (F14I)

In order to find out the pH stability of the mutant strain F14Y, the wild type and the mutant strain (F14Y) of lysine decarboxylase which completed protein refining were each soaked in various pH solution (pH 4.4, 5.6, 6.6, 7.6, 8.5 or 9.6), and stored at 4° C. for 21 days. As to the pH buffer solutions used, in the cases of pH 4.4 and 5.6, citric-sodium citrate buffer was used, in the cases of pH 6.6 and 7.6, potassium phosphate buffer was used, and in the cases of pH 8.5 and 9.6, borate buffer was used. After the storage for 21 days, the relative specific activity was measured, and the reaction was performed at pH 5.6 and temperature of 37° C. The reaction was analyzed through the HPLC analyzing method specified above. Moreover, the mean value of three experiments was taken. The results were shown in FIG. 4.

Figure 4:
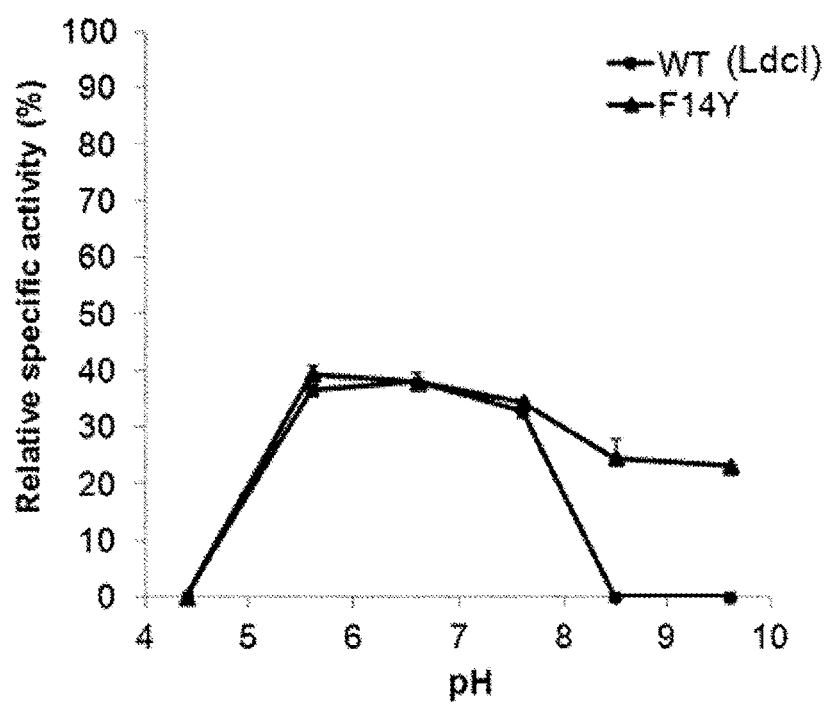
FIG. 4 is a comparative diagram of how much the activity is remaining after soaking the mutant strain wherein phenylalanine at position 14 of refined LdcI is substituted with tyrosine, and the refined wild type lysine decarbosylase LdcI in various pH solutions (pH 4.4, 5.6, 6.6, 7.6, 8.5 or 9.6). All of the values represent relative specific activities.

As shown in FIG. 4, there was not much difference as to the relative specific activities of the mutant strain and the wild type in the region of pH 4.4 to pH 7.6, and for example, all of the wild type and the mutant strain soaked in pH 5.6 preserved about 40% of activity. However, in the cases of pH 8.5 and 9.6, the wild type lost all of the specific activity, whereas the mutant strain in pH 8.5 had about 24.5%, and in pH 9.6 had about 23.2% of the activity left. Accordingly, it was found that the mutant strain has higher stability for pH.

Example 4: Thermal Stability Measurement of Lysine Decarboxylase Mutator (F14I)

After the wild type and the mutant strain (F14Y) of lysine decarboxylase which completed protein refining are continuously stored at 55° C., it was observed how much the activity of the enzyme decreased compared to the initial activity as time passes. The reaction was performed at pH 5.6 and 37° C. for 15 to 30 minutes, and the analysis was carried out by pH indicator analyzing method specified above. All of the results recorded the mean value of three experiments, and the results were shown in FIG. 5.

Figure 5:
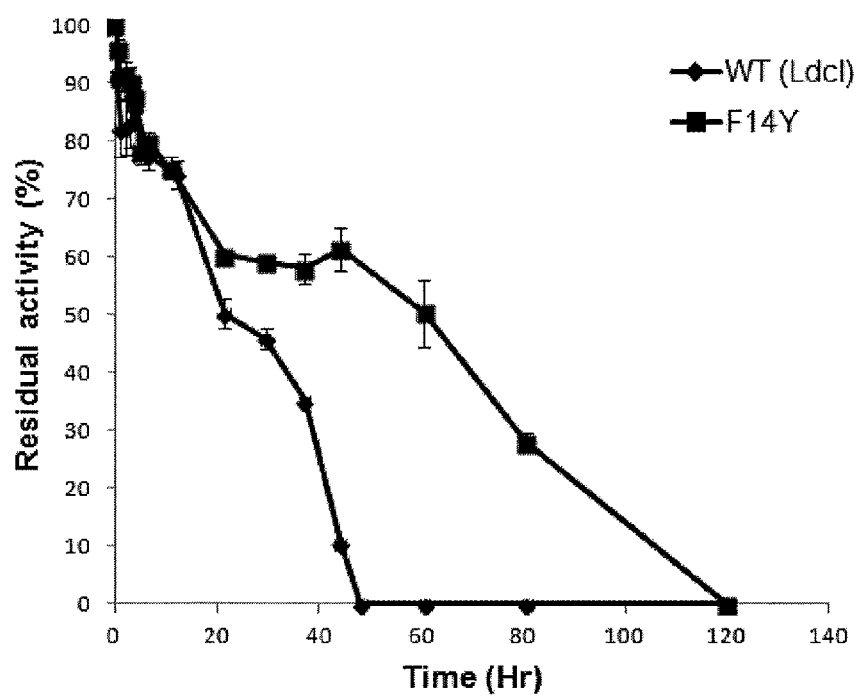
FIG. 5 is a comparative diagram of how much the relative activity decreased every hour, after storing the mutant strain wherein phenylalanine at position 14 of refined LdcI is substituted with tyrosine, and the refined wild type lysine decarbosylase LdcI at 55° C. All of the values represent relative specific activities.

As shown in FIG. 5, in the case of the wild type, all of activity disappeared after 48 hours. In contrast, in the case of F14Y mutant strain, about 61.4% of activity was left after 48 hours. In the case of the mutant strain, even if it is stored at 55° C. for 120 hours, about 1% of the activity is left. Accordingly, it was found that the mutant strain has higher thermal stability than the wild type.

Example 5: Observing Disulfide Bonding of the Lysine Decarboxylase Mutant Strain In order to observe the disulfide bonding of lysine decarboxylase mutant strain, the protein sizes when reducing power was applied and not applied to wild type lysine decarboxylase LdcI (SEQ ID NO: 15) and the mutant strain wherein phenylalanine at position 14 is substituted with cysteine, and lysine at position 44 is substituted with cysteine (F14C/K44C, SEQ ID NO: 6) were measured with SDS PAGE. Such a measurement can confirm whether a shared bond is formed between sulfur elements in a form —S—S— wherein two SH groups added to the mutant strain are producing in oxidation. In a reducing SDS PAGE, reducing power is applied to both of the wild type and the mutant strain to break all disulfides where bonding is possible, and then the sizes are observed, and in non-reducing SDS PAGE, it was observed whether disulfide bond is formed. The results were shown in FIG. 6.

Figure 6:
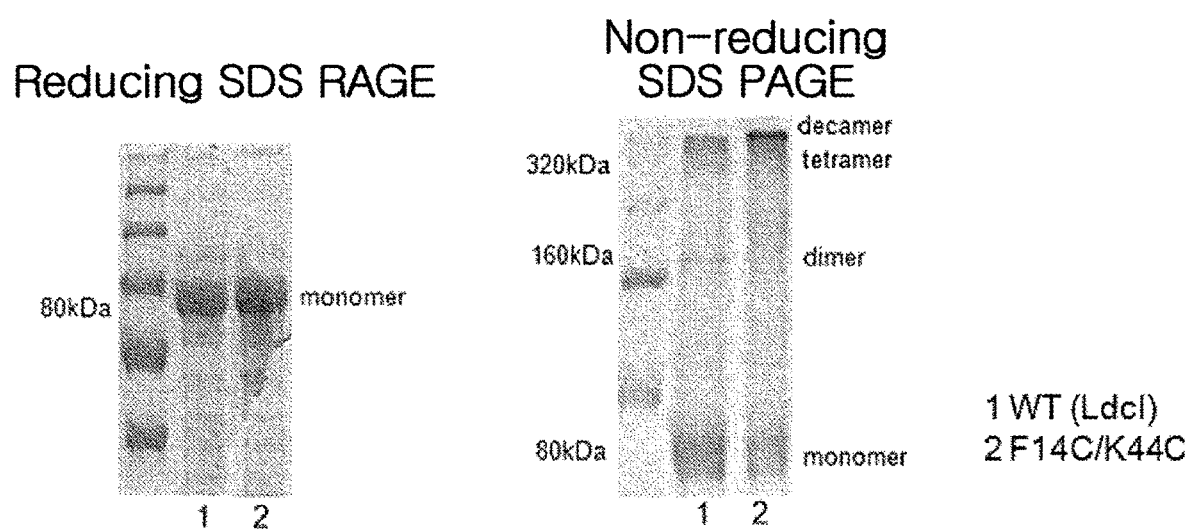
FIG. 6 shows the change in size of the protein by checking the size of the protein with SDS PAGE between when reducing power is applied and not applied to the wild type lysine decarboxylase LdcI and the mutant strain wherein phenylalanine at position 14 substituted with cysteine, and lysine at position 44 is substituted with cysteine of LdcI.

As shown in FIG. 6, it was observed that the wild type does not form disulfide bond through non-reducing and reducing SDS PAGE sizes. In contrast, in the case of the F14C/K44C mutant strain, it was observed that a decamer size was formed in non-reducing SDS and thereby it was observed that disulfide bond was stably formed.

Example 6: pH Stability Measurement of Lysine Decarboxylase Mutant Strain (F14C/K44C)

The wild type and the mutant strain (F14C/K44C) of lysine decarboxylase which completed protein refining were each soaked in alkali pH solution (pH 8, 9 or 10), and stored at 4° C. for 10 days. As to the pH buffer solutions used, in the cases of pH 8 and 9, borate buffer was used, and in the case of pH 10, sodium carbonate buffer was used. After storage for 10 days in each was stored in each pH, relative specific activity was measured, and the reaction was performed at pH 5.6 and temperature of 37° C. The reaction was analyzed through the HPLC analyzing method specified above. The results obtained from the mean value of three experiments were shown in FIG. 7.

Figure 7:
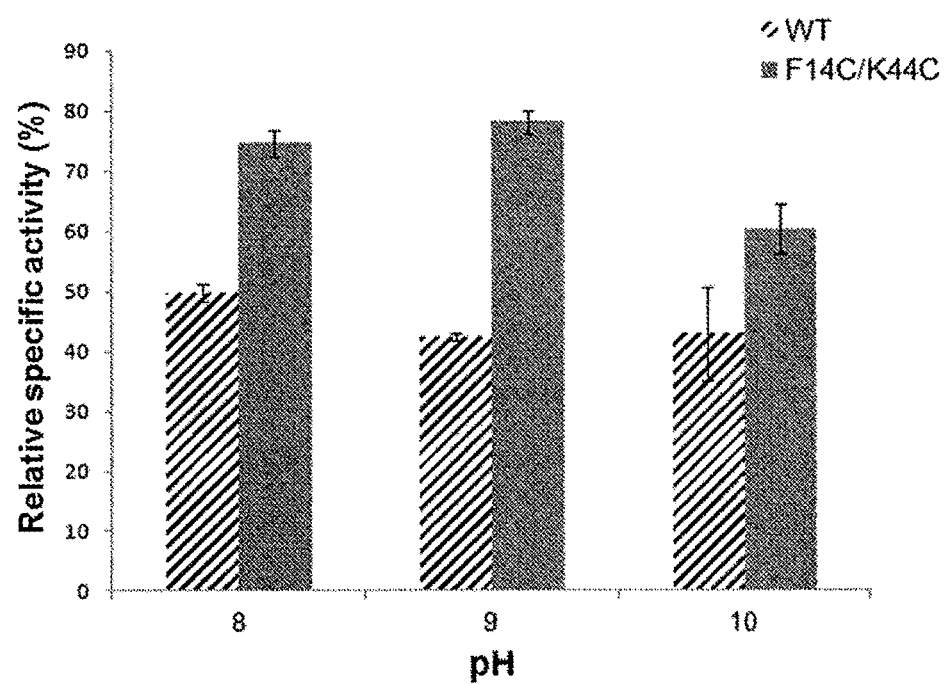
FIG. 7 is a comparative diagram of how much the activity is remaining after soaking refined wild type lysine decarboxylase LdcI and the mutant strain wherein phenylalanine at position 14 is substituted with cysteine, and lysine at position 44 is substituted with cysteine of refined LdcI in alkali pH solutions (pH 8, 9 or 10). All of the values represent relative specific activities.

As shown in FIG. 7, the wild type soaked in pH 8 preserved about 50% of activity. The mutant strain preserved about 75% of activity. The difference in pH stability between the two enzymes were clearly distinguished at pH 9.0, as 42% of activity was left for the wild type in the alkali pH, whereas about 78% of activity was left for the mutant strain in pH 9.0. Accordingly, it was observed that the mutant strain has higher stability for pH.

Example 7: Thermal Stability Measurement of Lysine Decarboxylase Mutant Strain (F14C/K44C)

After the wild type and the mutant strain (F14C/K44C) of lysine decarboxylase which completed protein refining are continuously stored at 60° C., it was observed how much the activity of the enzyme decreased compared to the initial activity as time passes. The reaction was performed at pH 5.6 and 37° C. for 15 to 30 minutes, and the analysis was carried out by pH indicator analyzing method specified above. All of the results recorded the mean value of three experiments, and the results were shown in FIG. 8.

Figure 8:
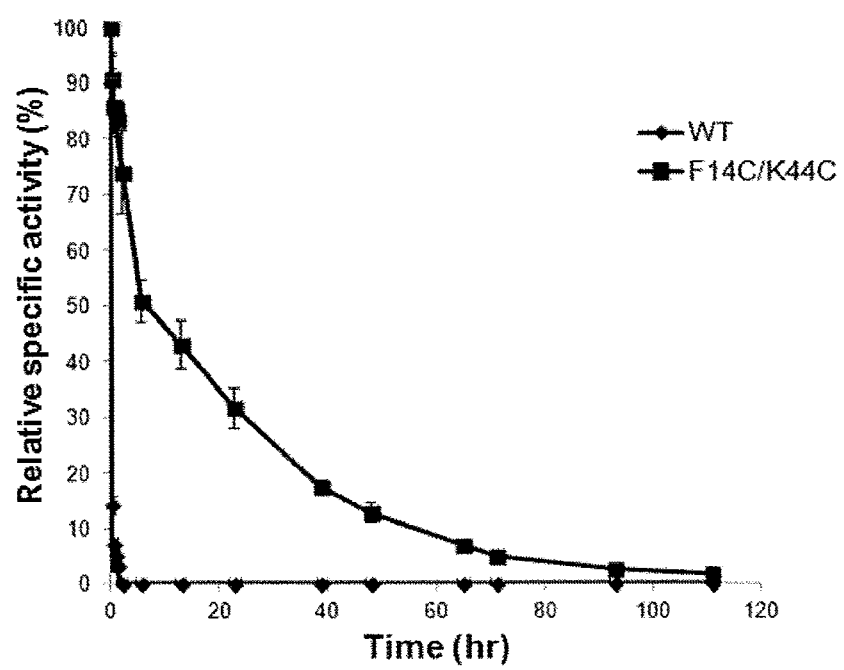
FIG. 8 is a comparative diagram of how much the relative activity decreased every hour, after storing refined wild lysine decarboxylase LdcI and the mutant strain wherein phenylalanine at position 14 substituted with cysteine, and lysine at position 44 is substituted with cysteine of refined LdcI at 60° C. All of the values represent relative specific activities.

As shown in FIG. 8, in the case of the wild type, 86% of activity disappeared after 10 minutes. In contrast, in the case of F14C/K44C mutant strain, about 50% of activity was left after 10 hours. In the case of the mutant strain, if it is stored at 60° C. for 2600 minutes, about 85% of activity disappears. Comparing the time spent for about 85% of activity disappearing for the wild type and the mutant strain, the wild type takes 10 minutes, and the mutant strain takes 2600 minutes, and thus it was found that the thermal stability of the mutant strain is 260 times higher than that of the wild type.

INDUSTRIAL APPLICABILITY

The present invention increases the production efficiency and productivity of cadaverine (1,5-diaminopentane) through use of mutant strain of lysine decarboxylase with improved catalytic function, and cadaverine is a material for use as a polymer precursor, and moreover, for various application in the field of chemical industry.

LIST OF SEQUENCES: FREE TEXT

SEQ ID NO: 1 is an amino acid sequence wherein phenylalanine at position 14 is substituted with tyrosine in the amino acid sequence of wild type LdcI, SEQ ID NO: 2 is an amino acid sequence wherein leucine at position 7 is substituted with methionine in the amino acid sequence of wild type LdcI, SEQ ID NO: 3 is an amino acid sequence wherein asparagine at position 8 is substituted with glycine in the amino acid sequence of wild type LdcI, SEQ ID NO: 4 is an amino acid sequence wherein leucine at position 7 is substituted with methionine, and asparagine at position 8 is substituted with glycine in the amino acid sequence of wild type LdcI, SEQ ID NO: 5 is an amino acid sequence wherein leucine at position 7 is substituted with methionine, asparagine at position 8 is substituted with glycine, and phenylalanine at position 14 is substituted with tyrosine in the amino acid sequence of wild type LdcI, SEQ ID NO: 6 is an amino acid sequence wherein phenylalanine at position 14 is substituted with cysteine and lysine at position 44 is substituted with cysteine in the amino acid sequence of wild type LdcI, SEQ ID NO: 7 is an amino acid sequence wherein leucine at position 7 is substituted with methionine, asparagine at position 8 is substituted with glycine, and lysine at position 44 is substituted with cysteine in the amino acid sequence of wild type LdcI, SEQ ID NO: 8 is a DNA sequence encoding the amino acid of SEQ ID NO:1, SEQ ID NO: 9 is a DNA sequence encoding the amino acid of SEQ ID NO: 2, SEQ ID NO: 10 is a DNA sequence encoding the amino acid of SEQ ID NO: 3, SEQ ID NO: 11 is a DNA sequence encoding the amino acid of SEQ ID NO: 4, SEQ ID NO: 12 is a DNA sequence encoding the amino acid of SEQ ID NO: 5, SEQ ID NO: 13 is a DNA sequence encoding the amino acid of SEQ ID NO: 6, SEQ ID NO: 14 is a DNA sequence encoding the amino acid of SEQ ID NO: 7, SEQ ID NO: 15 is an amino acid sequence of wild type LdcI.

The invention claimed is:

1. A lysine decarboxylase mutant comprising:
the amino acid sequence of SEQ ID NO: 4, wherein the leucine at position 7 in the amino acid sequence of SEQ ID NO: 15 (LdcI) is substituted with methionine, and the asparagine at position 8 in the amino acid sequence of SEQ ID NO: 15 (LdcI) is substituted with glycine (L7M/N8G);
the amino acid sequence of SEQ ID NO: 5, wherein the leucine at position 7 in the amino acid sequence of SEQ ID NO: 15 (LdcI) is substituted with methionine, the asparagine at position 8 in the amino acid sequence of SEQ ID NO: 15 (LdcI) is substituted with glycine, and the phenylalanine at position 14 in the amino acid sequence of SEQ ID NO: 15 (LdcI) is substituted with tyrosine (L7M/N8G/F14Y);
the amino acid sequence of SEQ ID NO: 6, wherein the phenylalanine at position 14 in the amino acid sequence of SEQ ID NO: 15 (LdcI) is substituted with cysteine, and the lysine at position 44 in the amino acid sequence of SEQ ID NO: 15 (LdcI) is substituted with cysteine (F14C/K44C); or
the amino acid sequence of SEQ ID NO: 7, wherein the leucine at position 7 in the amino acid sequence of SEQ ID NO: 15 (LdcI) is substituted with methionine, the asparagine at position 8 in the amino acid sequence of SEQ ID NO: 15 (LdcI) is substituted with glycine, the phenylalanine at position 14 in the amino acid sequence of SEQ ID NO: 15 (LdcI) is substituted with cysteine, and the lysine at position 44 in the amino acid sequence of SEQ ID NO: 15 (LdcI) is substituted with cysteine (L7M/N8G/F14C/K44C).

2. A DNA encoding the lysine decarboxylase mutant according to claim 1.

3. The DNA according to claim 2 comprising the sequence of any one of SEQ ID NOS: 11 to 14.

4. A recombinant DNA vector comprising the DNA according to claim 2.

5. A host cell transformed with the recombinant DNA vector according to claim 4.

6. An extract of a host cell transformed with the recombinant DNA vector according to claim 4.

7. A method for producing cadaverine, comprising:
contacting a host cell transformed with the recombinant DNA vector according to claim 4 with starch, glucose, or lysine by culturing the host cell in the presence of starch, glucose, or lysine; or
contacting an extract of the host cell with lysine.

8. The method for producing cadaverine according to claim 7, wherein the host cell is contacted with glucose by culturing the host cell in the presence of glucose.

9. The method for producing cadaverine according to claim 7, wherein the host cell or extract is contacted with lysine at a concentration 1M to 6M, wherein contacting the host cell with the lysine comprises culturing the host cell in the presence of the lysine.

* * * * *

SEQUENCE LISTING

<160> NUMBER OF SEQ ID NOS: 15

<210> SEQ ID NO 1
<211> LENGTH: 715
<212> TYPE: PRT
<213> ORGANISM: Escherichia coli

<400> SEQUENCE: 1

Met Asn Val Ile Ala Ile Leu Asn His Met Gly Val Tyr Tyr Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

```
Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Ser Lys Lys
705                 710                 715

<210> SEQ ID NO 2
<211> LENGTH: 715
<212> TYPE: PRT
<213> ORGANISM: Escherichia coli

<400> SEQUENCE: 2

Met Asn Val Ile Ala Ile Met Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30
```

```
Ile Val Tyr Pro Asn Asp Arg Asp Asp Leu Leu Lys Leu Ile Glu Asn
             35                  40                  45

Asn Ala Arg Leu Cys Gly Val Ile Phe Asp Trp Asp Lys Tyr Asn Leu
 50                      55                  60

Glu Leu Cys Glu Glu Ile Ser Lys Met Asn Glu Asn Leu Pro Leu Tyr
 65                      70                  75                  80

Ala Phe Ala Asn Thr Tyr Ser Thr Leu Asp Val Ser Leu Asn Asp Leu
                 85                  90                  95

Arg Leu Gln Ile Ser Phe Phe Glu Tyr Ala Leu Gly Ala Ala Glu Asp
                100                 105                 110

Ile Ala Asn Lys Ile Lys Gln Thr Thr Asp Glu Tyr Ile Asn Thr Ile
                115                 120                 125

Leu Pro Pro Leu Thr Lys Ala Leu Phe Lys Tyr Val Arg Glu Gly Lys
            130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
            210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445
```

```
Trp Phe Phe Asp Val Trp Gln Pro Asp His Ile Asp Thr Thr Glu Cys
450                 455                 460
Trp Pro Leu Arg Ser Asp Ser Thr Trp His Gly Phe Lys Asn Ile Asp
465                 470                 475                 480
Asn Glu His Met Tyr Leu Asp Pro Ile Lys Val Thr Leu Leu Thr Pro
                485                 490                 495
Gly Met Glu Lys Asp Gly Thr Met Ser Asp Phe Gly Ile Pro Ala Ser
            500                 505                 510
Ile Val Ala Lys Tyr Leu Asp Glu His Gly Ile Val Val Glu Lys Thr
            515                 520                 525
Gly Pro Tyr Asn Leu Leu Phe Leu Phe Ser Ile Gly Ile Asp Lys Thr
            530                 535                 540
Lys Ala Leu Ser Leu Leu Arg Ala Leu Thr Asp Phe Lys Arg Ala Phe
545                 550                 555                 560
Asp Leu Asn Leu Arg Val Lys Asn Met Leu Pro Ser Leu Tyr Arg Glu
                565                 570                 575
Asp Pro Glu Phe Tyr Glu Asn Met Arg Ile Gln Glu Leu Ala Gln Asn
                580                 585                 590
Ile His Lys Leu Ile Val His His Asn Leu Pro Asp Leu Met Tyr Arg
                595                 600                 605
Ala Phe Glu Val Leu Pro Thr Met Val Met Thr Pro Tyr Ala Ala Phe
            610                 615                 620
Gln Lys Glu Leu His Gly Met Thr Glu Glu Val Tyr Leu Asp Glu Met
625                 630                 635                 640
Val Gly Arg Ile Asn Ala Asn Met Ile Leu Pro Tyr Pro Pro Gly Val
                645                 650                 655
Pro Leu Val Met Pro Gly Glu Met Ile Thr Glu Glu Ser Arg Pro Val
            660                 665                 670
Leu Glu Phe Leu Gln Met Leu Cys Glu Ile Gly Ala His Tyr Pro Gly
            675                 680                 685
Phe Glu Thr Asp Ile His Gly Ala Tyr Arg Gln Ala Asp Gly Arg Tyr
            690                 695                 700
Thr Val Lys Val Leu Lys Glu Glu Ser Lys Lys
705                 710                 715

<210> SEQ ID NO 3
<211> LENGTH: 715
<212> TYPE: PRT
<213> ORGANISM: Escherichia coli

<400> SEQUENCE: 3

Met Asn Val Ile Ala Ile Leu Gly His Met Gly Val Tyr Phe Lys Glu
1               5                   10                  15
Glu Pro Ile Arg Glu Leu His Arg Ala Leu Glu Arg Leu Asn Phe Gln
                20                  25                  30
Ile Val Tyr Pro Asn Asp Arg Asp Leu Leu Lys Leu Ile Glu Asn
                35                  40                  45
Asn Ala Arg Leu Cys Gly Val Ile Phe Asp Trp Asp Lys Tyr Asn Leu
            50                  55                  60
Glu Leu Cys Glu Glu Ile Ser Lys Met Asn Glu Asn Leu Pro Leu Tyr
65                  70                  75                  80
Ala Phe Ala Asn Thr Tyr Ser Thr Leu Asp Val Ser Leu Asn Asp Leu
                85                  90                  95
Arg Leu Gln Ile Ser Phe Phe Glu Tyr Ala Leu Gly Ala Ala Glu Asp
                100                 105                 110
```

```
Ile Ala Asn Lys Ile Lys Gln Thr Thr Asp Glu Tyr Ile Asn Thr Ile
            115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525
```

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
            595                 600                 605

Ala Phe Glu Val Leu Pro Thr Met Val Met Thr Pro Tyr Ala Ala Phe
610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
690                 695                 700

Thr Val Lys Val Leu Lys Glu Glu Ser Lys Lys
705                 710                 715

<210> SEQ ID NO 4
<211> LENGTH: 715
<212> TYPE: PRT
<213> ORGANISM: Escherichia coli

<400> SEQUENCE: 4

Met Asn Val Ile Ala Ile Met Gly His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
            35                  40                  45

Asn Ala Arg Leu Cys Gly Val Ile Phe Asp Trp Asp Lys Tyr Asn Leu
50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
            115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

```
His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
        210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
        290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
        450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605
```

```
Ala Phe Glu Val Leu Pro Thr Met Val Met Thr Pro Tyr Ala Ala Phe
610                 615                 620

Gln Lys Glu Leu His Gly Met Thr Glu Val Tyr Leu Asp Glu Met
625                 630                 635                 640

Val Gly Arg Ile Asn Ala Asn Met Ile Leu Pro Tyr Pro Gly Val
            645                 650                 655

Pro Leu Val Met Pro Gly Glu Met Ile Thr Glu Ser Arg Pro Val
            660                 665                 670

Leu Glu Phe Leu Gln Met Leu Cys Glu Ile Gly Ala His Tyr Pro Gly
                675                 680                 685

Phe Glu Thr Asp Ile His Gly Ala Tyr Arg Gln Ala Asp Gly Arg Tyr
                690                 695                 700

Thr Val Lys Val Leu Lys Glu Glu Ser Lys Lys
705                 710                 715

<210> SEQ ID NO 5
<211> LENGTH: 715
<212> TYPE: PRT
<213> ORGANISM: Escherichia coli

<400> SEQUENCE: 5

Met Asn Val Ile Ala Ile Met Gly His Met Gly Val Tyr Tyr Lys Glu
1               5                   10                  15

Glu Pro Ile Arg Glu Leu His Arg Ala Leu Glu Arg Leu Asn Phe Gln
                20                  25                  30

Ile Val Tyr Pro Asn Asp Arg Asp Leu Leu Lys Leu Ile Glu Asn
                35              40                  45

Asn Ala Arg Leu Cys Gly Val Ile Phe Asp Trp Asp Lys Tyr Asn Leu
50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
                100                 105                 110

Ile Ala Asn Lys Ile Lys Gln Thr Thr Asp Glu Tyr Ile Asn Thr Ile
                115                 120                 125

Leu Pro Pro Leu Thr Lys Ala Leu Phe Lys Tyr Val Arg Glu Gly Lys
            130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Gln Tyr Ile Ala Arg Val Phe
                195                 200                 205

Asn Ala Asp Arg Ser Tyr Met Val Thr Asn Gly Thr Ser Thr Ala Asn
                210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270
```

```
Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
                370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
                450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
                530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
                595                 600                 605

Ala Phe Glu Val Leu Pro Thr Met Val Met Thr Pro Tyr Ala Ala Phe
                610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
                675                 680                 685
```

```
Phe Glu Thr Asp Ile His Gly Ala Tyr Arg Gln Ala Asp Gly Arg Tyr
690                 695                 700

Thr Val Lys Val Leu Lys Glu Glu Ser Lys Lys
705                 710                 715

<210> SEQ ID NO 6
<211> LENGTH: 715
<212> TYPE: PRT
<213> ORGANISM: Escherichia coli

<400> SEQUENCE: 6

Met Asn Val Ile Ala Ile Leu Asn His Met Gly Val Tyr Cys Lys Glu
1               5                   10                  15

Glu Pro Ile Arg Glu Leu His Arg Ala Leu Glu Arg Leu Asn Phe Gln
                20                  25                  30

Ile Val Tyr Pro Asn Asp Arg Asp Asp Leu Leu Cys Leu Ile Glu Asn
            35                  40                  45

Asn Ala Arg Leu Cys Gly Val Ile Phe Asp Trp Asp Lys Tyr Asn Leu
        50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350
```

Arg Val Glu Gly Lys Val Ile Tyr Glu Thr Gln Ser Thr His Lys Leu
    355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
        450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
            595                 600                 605

Ala Phe Glu Val Leu Pro Thr Met Val Met Thr Pro Tyr Ala Ala Phe
        610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
        690                 695                 700

Thr Val Lys Val Leu Lys Glu Glu Ser Lys Lys
705                 710                 715

<210> SEQ ID NO 7
<211> LENGTH: 715
<212> TYPE: PRT
<213> ORGANISM: Escherichia coli

<400> SEQUENCE: 7

Met Asn Val Ile Ala Ile Met Gly His Met Gly Val Tyr Cys Lys Glu

-continued

```
1               5                   10                  15
Glu Pro Ile Arg Glu Leu His Arg Ala Leu Glu Arg Leu Asn Phe Gln
            20                  25                  30
Ile Val Tyr Pro Asn Asp Arg Asp Leu Leu Cys Leu Ile Glu Asn
            35                  40                  45
Asn Ala Arg Leu Cys Gly Val Ile Phe Asp Trp Asp Lys Tyr Asn Leu
50                  55                  60
Glu Leu Cys Glu Glu Ile Ser Lys Met Asn Glu Asn Leu Pro Leu Tyr
65                  70                  75                  80
Ala Phe Ala Asn Thr Tyr Ser Thr Leu Asp Val Ser Leu Asn Asp Leu
                85                  90                  95
Arg Leu Gln Ile Ser Phe Phe Glu Tyr Ala Leu Gly Ala Ala Glu Asp
                100                 105                 110
Ile Ala Asn Lys Ile Lys Gln Thr Thr Asp Glu Tyr Ile Asn Thr Ile
                115                 120                 125
Leu Pro Pro Leu Thr Lys Ala Leu Phe Lys Tyr Val Arg Glu Gly Lys
            130                 135                 140
Tyr Thr Phe Cys Thr Pro Gly His Met Gly Gly Thr Ala Phe Gln Lys
145                 150                 155                 160
Ser Pro Val Gly Ser Leu Phe Tyr Asp Phe Phe Gly Pro Asn Thr Met
                165                 170                 175
Lys Ser Asp Ile Ser Ile Ser Val Ser Glu Leu Gly Ser Leu Leu Asp
                180                 185                 190
His Ser Gly Pro His Lys Glu Ala Glu Gln Tyr Ile Ala Arg Val Phe
            195                 200                 205
Asn Ala Asp Arg Ser Tyr Met Val Thr Asn Gly Thr Ser Thr Ala Asn
210                 215                 220
Lys Ile Val Gly Met Tyr Ser Ala Pro Ala Gly Ser Thr Ile Leu Ile
225                 230                 235                 240
Asp Arg Asn Cys His Lys Ser Leu Thr His Leu Met Met Met Ser Asp
                245                 250                 255
Val Thr Pro Ile Tyr Phe Arg Pro Thr Arg Asn Ala Tyr Gly Ile Leu
            260                 265                 270
Gly Gly Ile Pro Gln Ser Glu Phe Gln His Ala Thr Ile Ala Lys Arg
            275                 280                 285
Val Lys Glu Thr Pro Asn Ala Thr Trp Pro Val His Ala Val Ile Thr
290                 295                 300
Asn Ser Thr Tyr Asp Gly Leu Leu Tyr Asn Thr Asp Phe Ile Lys Lys
305                 310                 315                 320
Thr Leu Asp Val Lys Ser Ile His Phe Asp Ser Ala Trp Val Pro Tyr
                325                 330                 335
Thr Asn Phe Ser Pro Ile Tyr Glu Gly Lys Cys Gly Met Ser Gly Gly
            340                 345                 350
Arg Val Glu Gly Lys Val Ile Tyr Glu Thr Gln Ser Thr His Lys Leu
            355                 360                 365
Leu Ala Ala Phe Ser Gln Ala Ser Met Ile His Val Lys Gly Asp Val
            370                 375                 380
Asn Glu Glu Thr Phe Asn Glu Ala Tyr Met Met His Thr Thr Thr Ser
385                 390                 395                 400
Pro His Tyr Gly Ile Val Ala Ser Thr Glu Thr Ala Ala Ala Met Met
                405                 410                 415
Lys Gly Asn Ala Gly Lys Arg Leu Ile Asn Gly Ser Ile Glu Arg Ala
            420                 425                 430
```

```
Ile Lys Phe Arg Lys Glu Ile Lys Arg Leu Arg Thr Glu Ser Asp Gly
        435                 440                 445

Trp Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 8
<211> LENGTH: 2148
<212> TYPE: DNA
<213> ORGANISM: Escherichia coli

<400> SEQUENCE: 8
atgaacgtta ttgcaatatt gaatcacatg ggggtttatt ataaagaaga acccatccgt     60
gaacttcatc gcgcgcttga acgtctgaac ttccagattg tttacccgaa cgaccgtgac    120 gactattaa aactgatcga aaacaatgcg cgtctgtgcg gcgttatttt tgactgggat    180
aaatataatc tcgagctgtg cgaagaaatt agcaaaatga cgagaaccct gccgttgtac    240
gcgttcgcta atacgtattc cactctcgat gtaagcctga tgacctgcg tttacagatt    300 agcttctttg aatatgcgct gggtgctgct gaagatattg ctaataagat caagcagacc    360
actgacgaat atatcaacac tattctgcct ccgctgacta agcactgtt taaatatgtt    420 cgtgaaggta aatatacttt ctgtactcct ggtcacatgg gcggtactgc attccagaaa    480
```

```
agcccggtag gtagcctgtt ctatgatttc tttggtccga ataccatgaa atctgatatt      540
tccatttcag tatctgaact gggttctctg ctggatcaca gtggtccaca caaagaagca      600
gaacagtata tcgctcgcgt ctttaacgca gaccgcagct acatggtgac caacggtact      660
tccactgcga acaaaattgt tggtatgtac tctgctccgg caggcagcac cattctgatt      720
gaccgtaact gccacaaatc gctgacccac ctgatgatga tgagcgatgt tacgccaatc      780
tatttccgcc cgacccgtaa cgcttacggt attcttggtg gtatcccaca gagtgaattc      840
cagcacgcta ccattgctaa gcgcgtgaaa gaaacaccaa acgcaacctg gccggtacat      900
gctgtaatta ccaactctac ctatgatggt ctgctgtaca caccgacttt catcaagaaa      960
acactggatg tgaaatccat ccactttgac tccgcgtggg tgccttacac caacttctca     1020
ccgatttacg aaggtaaatg cggtatgagc ggtggccgtg tagaagggaa agtgatttac     1080
gaaacccagt ccactcacaa actgctggcg gcgttctctc aggcttccat gatccacgtt     1140
aaaggtgacg taaacgaaga aacctttaac gaagcctaca tgatgcacac caccacttct     1200
ccgcactacg gtatcgtggc gtccactgaa accgctgcgg cgatgatgaa gggtaatgct     1260
ggtaagcgtc tgatcaacgg ttccattgaa cgtgcgatca aattccgtaa agagatcaaa     1320
cgtctgagaa cggaatctga tggctggttc tttgatgttt ggcagccgga tcatatcgat     1380
acgactgaat gctggccgct gcgttctgac agcacctggc acggcttcaa aaacatcgat     1440
aacgagcaca tgtatcttga cccgatcaaa gtcaccctgc tgactccggg gatggaaaaa     1500
gacggcacca tgagcgactt tggtattccg gccagcatcg tggcgaaata cctcgacgaa     1560
catggcatcg ttgttgagaa aaccggtccg tataacctgc tgttcctgtt cagcatcggt     1620
atcgataaga ccaaagcact gagcctgctg cgtgctctga ctgacttcaa acgtgcgttc     1680
gacctgaacc tgcgtgtgaa aaacatgctg ccgtctctgt atcgtgaaga tcctgaattc     1740
tatgaaaaca tgcgtattca ggaactggct caaaatatcc acaaactgat tgttcaccac     1800
aatctgccgg atctgatgta tcgcgcattt gaagtgctgc cgacgatggt aatgactccg     1860
tatgctgcgt tccagaaaga gctgcacggt atgaccgaag aagtttacct cgacgaaatg     1920
gtaggtcgta ttaacgccaa tatgatcctt ccgtatccgc cggagttcc tctggtaatg     1980 ccgggtgaaa tgatcaccga agaaagccgt ccggttctgg agttcctgca gatgctgtgt     2040
gaaatcggcg ctcactatcc gggctttgaa accgatattc acggtgcata ccgtcaggct     2100
gatggccgct ataccgttaa ggtattgaaa gaagaaagca aaaaataa                  2148
```

<210> SEQ ID NO 9
<211> LENGTH: 2148
<212> TYPE: DNA
<213> ORGANISM: Escherichia coli

<400> SEQUENCE: 9

```
atgaacgtta ttgcaataat gaatcacatg ggggtttatt ttaaagaaga acccatccgt       60
gaacttcatc gcgcgcttga acgtctgaac ttccagattg tttacccgaa cgaccgtgac      120
gacttattaa aactgatcga aaacaatgcg cgtctgtgcg gcgttatttt tgactgggat      180
aaatataatc tcgagctgtg cgaagaaatt agcaaaatga acgagaacct gccgttgtac      240
gcgttcgcta atacgtattc cactctcgat gtaagcctga tgacctgcg tttacagatt      300 agcttctttg aatatgcgct gggtgctgct gaagatattg ctaataagat caagcagacc      360
actgacgaat atatcaacac tattctgcct ccgctgacta agcactgtt taaatatgtt      420 cgtgaaggta atatactttt ctgtactcct ggtcacatgg gcggtactgc attccagaaa      480
```

```
agcccggtag gtagcctgtt ctatgatttc tttggtccga ataccatgaa atctgatatt    540
tccatttcag tatctgaact gggttctctg ctggatcaca gtggtccaca caaagaagca    600
gaacagtata tcgctcgcgt cttaacgca gaccgcagct acatggtgac caacggtact    660
tccactgcga acaaaattgt tggtatgtac tctgctccgg caggcagcac cattctgatt    720
gaccgtaact gccacaaatc gctgacccac ctgatgatga tgagcgatgt tacgccaatc    780
tatttccgcc cgaccgtaa cgcttacggt attcttggtg gtatcccaca gagtgaattc    840
cagcacgcta ccattgctaa gcgcgtgaaa gaaacaccaa acgcaacctg ccggtacat    900 gctgtaatta ccaactctac ctatgatggt ctgctgtaca acccgactt catcaagaaa    960 acactggatg tgaaatccat ccactttgac tccgcgtggg tgccttacac caacttctca   1020
ccgatttacg aaggtaaatg cggtatgagc ggtggccgtg tagaagggaa agtgattttac   1080 gaaacccagt ccactcacaa actgctggcg gcgttctctc aggcttccat gatccacgtt   1140
aaaggtgaca taaacgaaga aaccttaac gaagcctaca tgatgcacac caccacttct   1200
ccgcactacg gtatcgtggc gtccactgaa accgctgcgg cgatgatgaa gggtaatgct   1260
ggtaagcgtc tgatcaacgg ttccattgaa cgtgcgatca aattccgtaa agagatcaaa   1320
cgtctgagaa cggaatctga tggctggttc tttgatgttt ggcagccgga tcatatcgat   1380
acgactgaat gctggccgct gcgttctgac agcacctggc acggcttcaa aaacatcgat   1440
aacgagcaca tgtatcttga cccgatcaaa gtcaccctgc tgactccggg gatggaaaaa   1500
gacggcacca tgagcgactt tggtattccg ccagcatcg tggcgaaata cctcgacgaa   1560
catggcatcg ttgttgagaa aaccggtccg tataacctgc tgttcctgtt cagcatcggt   1620
atcgataaga ccaaagcact gagcctgctg cgtgctctga ctgacttcaa acgtgcgttc   1680
gacctgaacc tgcgtgtgaa aaacatgctg ccgtctctgt atcgtgaaga tcctgaattc   1740
tatgaaaaca tgcgtattca ggaactggct caaaatatcc acaaactgat tgttcaccac   1800
aatctgccgg atctgatgta tcgcgcattt gaagtgctgc cgacgatggt aatgactccg   1860
tatgctgcgt tccagaaaga gctgcacggt atgaccgaag aagtttacct cgacgaaatg   1920
gtaggtcgta ttaacgccaa tatgatcctt ccgtatccgc cgggagttcc tctggtaatg   1980
ccgggtgaaa tgatcaccga agaaagccgt ccggttctgg agttcctgca gatgctgtgt   2040
gaaatcggcg ctcactatcc gggctttgaa accgatattc acgtgcata ccgtcaggct   2100 gatggccgct ataccgttaa ggtattgaaa gaagaaagca aaaaataa                2148
```

<210> SEQ ID NO 10
<211> LENGTH: 2148
<212> TYPE: DNA
<213> ORGANISM: Escherichia coli

<400> SEQUENCE: 10

```
atgaacgtta ttgcaatatt gggacacatg ggggtttatt ttaaagaaga acccatccgt     60
gaacttcatc gcgcgcttga acgtctgaac ttccagattg tttacccgaa cgaccgtgac    120
gacttattaa aactgatcga aaacaatgcg cgtctgtgcg gcgttatttt tgactgggat    180
aaatataatc tcgagctgtg cgaagaaatt agcaaaatga acgagaacct gccgttgtac    240
gcgttcgcta atacgtattc cactctcgat gtaagcctga tgacctgcg tttacagatt    300 agcttctttg aatatgcgct gggtgctgct gaagatattg ctaataagat caagcagacc    360
actgacgaat atatcaacac tattctgcct ccgctgacta agcactgtt taaatatgtt    420
```

-continued

```
cgtgaaggta aatatacttt ctgtactcct ggtcacatgg gcggtactgc attccagaaa      480
agcccggtag gtagcctgtt ctatgatttc tttggtccga ataccatgaa atctgatatt      540
tccatttcag tatctgaact gggttctctg ctggatcaca gtggtccaca caaagaagca      600
gaacagtata tcgctcgcgt ctttaacgca gaccgcagct acatggtgac caacggtact      660
tccactgcga acaaaattgt tggtatgtac tctgctccgg caggcagcac cattctgatt      720
gaccgtaact gccacaaatc gctgacccac ctgatgatga tgagcgatgt tacgccaatc      780
tatttccgcc cgaccgtaa cgcttacggt attcttggtg gtatcccaca gagtgaattc       840
cagcacgcta ccattgctaa gcgcgtgaaa gaaacaccaa acgcaacctg gccggtacat      900
gctgtaatta ccaactctac ctatgatggt ctgctgtaca acaccgactt catcaagaaa      960
acactggatg tgaaatccat ccactttgac tccgcgtggg tgccttacac caacttctca      1020
ccgatttacg aaggtaaatg cggtatgagc ggtggccgtg tagaagggaa agtgatttac      1080
gaaacccagt ccactcacaa actgctggcg gcgttctctc aggcttccat gatccacgtt      1140
aaaggtgacg taaacgaaga aacctttaac gaagcctaca tgatgcacac caccacttct      1200
ccgcactacg gtatcgtggc gtccactgaa accgctgcgg cgatgatgaa gggtaatgct      1260
ggtaagcgtc tgatcaacgg ttccattgaa cgtgcgatca aattccgtaa agagatcaaa      1320
cgtctgagaa cggaatctga tggctggttc tttgatgttt ggcagccgga tcatatcgat      1380
acgactgaat gctggccgct gcgttctgac agcacctggc acggcttcaa aaacatcgat      1440
aacgagcaca tgtatcttga cccgatcaaa gtcaccctgc tgactccggg gatggaaaaa      1500
gacggcacca tgagcgactt tggtattccg gccagcatcg tggcgaaata cctcgacgaa      1560
catggcatcg ttgttgagaa accggtccg tataacctgc tgttcctgtt cagcatcggt      1620
atcgataaga ccaaagcact gagcctgctg cgtgctctga ctgacttcaa acgtgcgttc      1680
gacctgaacc tgcgtgtgaa aaacatgctg ccgtctctgt atcgtgaaga tcctgaattc      1740
tatgaaaaca tgcgtattca ggaactggct caaaatatcc acaaactgat tgttcaccac      1800
aatctgccgg atctgatgta tcgcgcattt gaagtgctgc cgacgatggt aatgactccg      1860
tatgctgcgt tccagaaaga gctgcacggt atgaccgaag aagtttacct cgacgaaatg      1920
gtaggtcgta ttaacgccaa tatgatcctt ccgtatccgc cgggagttcc tctggtaatg      1980
ccgggtgaaa tgatcaccga agaaagccgt ccggttctgg agttcctgca gatgctgtgt      2040
gaaatcggcg ctcactatcc gggctttgaa accgatattc acggtgcata ccgtcaggct      2100
gatggccgct ataccgttaa ggtattgaaa gaagaaagca aaaaataa                   2148
```

<210> SEQ ID NO 11
<211> LENGTH: 2148
<212> TYPE: DNA
<213> ORGANISM: Escherichia coli

<400> SEQUENCE: 11

```
atgaacgtta ttgcaataat gggacacatg ggggtttatt ttaaagaaga acccatccgt       60
gaacttcatc gcgcgcttga acgtctgaac ttccagattg tttacccgaa cgaccgtgac      120 gactattaa aactgatcga aaacaatgcg cgtctgtgcg gcgttatttt tgactgggat      180
aaatataatc tcgagctgtg cgaagaaatt agcaaaatga acgagaacct gccgttgtac      240
gcgttcgcta atacgtattc cactctcgat gtaagcctga tgacctgcg tttacagatt      300 agcttctttg aatatgcgct gggtgctgct gaagatattg ctaataagat caagcagacc      360
actgacgaat atatcaacac tattctgcct ccgctgacta agcactgtt taaatatgtt      420
```

```
cgtgaaggta aatatacttt ctgtactcct ggtcacatgg gcggtactgc attccagaaa      480
agcccggtag gtagcctgtt ctatgatttc tttggtccga ataccatgaa atctgatatt      540
tccatttcag tatctgaact gggttctctg ctggatcaca gtggtccaca caagaagca       600 gaacagtata tcgctcgcgt ctttaacgca gaccgcagct acatggtgac caacggtact      660
tccactgcga acaaaattgt tggtatgtac tctgctccgg caggcagcac cattctgatt      720
gaccgtaact gccacaaatc gctgacccac ctgatgatga tgagcgatgt tacgccaatc      780
tatttccgcc cgacccgtaa cgcttacggt attcttggtg gtatcccaca gagtgaattc      840
cagcacgcta ccattgctaa gcgcgtgaaa gaaacaccaa acgcaacctg gccggtacat      900
gctgtaatta ccaactctac ctatgatggt ctgctgtaca caccgactt catcaagaaa       960 acactggatg tgaaatccat ccactttgac tccgcgtggg tgccttacac caacttctca     1020
ccgatttacg aaggtaaatg cggtatgagc ggtggccgtg tagaagggaa agtgatttac     1080
gaaacccagt ccactcacaa actgctggcg gcgttctctc aggcttccat gatccacgtt     1140
aaaggtgacg taaacgaaga aacctttaac gaagcctaca tgatgcacac caccacttct     1200
ccgcactacg gtatcgtggc gtccactgaa accgctgcgg cgatgatgaa gggtaatgct     1260
ggtaagcgtc tgatcaacgg ttccattgaa cgtgcgatca aattccgtaa agagatcaaa     1320
cgtctgagaa cggaatctga tggctggttc tttgatgttt ggcagccgga tcatatcgat     1380
acgactgaat gctggccgct gcgttctgac agcacctggc acggcttcaa aaacatcgat     1440
aacgagcaca tgtatcttga cccgatcaaa gtcaccctgc tgactccggg gatggaaaaa     1500
gacggcacca tgagcgactt tggtattccg gccagcatcg tggcgaaata cctcgacgaa     1560
catggcatcg ttgttgagaa aaccggtccg tataacctgc tgttcctgtt cagcatcggt     1620
atcgataaga ccaaagcact gagcctgctg cgtgctctga ctgacttcaa acgtgcgttc     1680
gacctgaacc tgcgtgtgaa aaacatgctg ccgtctctgt atcgtgaaga tcctgaattc     1740
tatgaaaaca tgcgtattca ggaactggct caaaatatcc acaaactgat tgttcaccac     1800
aatctgccgg atctgatgta tcgcgcattt gaagtgctgc cgacgatggt aatgactccg     1860
tatgctgcgt tccagaaaga gctgcacggt atgaccgaag aagtttacct cgacgaaatg     1920
gtaggtcgta ttaacgccaa tatgatcctt ccgtatccgc cgggagttcc tctggtaatg     1980
ccgggtgaaa tgatcaccga agaaagccgt ccggttctgg agttcctgca gatgctgtgt     2040
gaaatcggcg ctcactatcc gggctttgaa accgatattc acggtgcata ccgtcaggct     2100
gatggccgct ataccgttaa ggtattgaaa gaagaaagca aaaaataa                  2148
```

<210> SEQ ID NO 12
<211> LENGTH: 2148
<212> TYPE: DNA
<213> ORGANISM: Escherichia coli

<400> SEQUENCE: 12

```
atgaacgtta ttgcaataat gggacacatg ggggtttatt ataaagaaga acccatccgt       60
gaacttcatc gcgcgcttga acgtctgaac ttccagattg tttacccgaa cgaccgtgac      120
gacttattaa aactgatcga aaacaatgcg cgtctgtgcg gcgttatttt tgactgggat      180
aaatataatc tcgagctgtg cgaagaaatt agcaaaatga acgagaacct gccgttgtac      240
gcgttcgcta atacgtattc cactctcgat gtaagcctga atgacctgcg tttacagatt      300
agcttctttg aatatgcgct gggtgctgct gaagatattg ctaataagat caagcagacc      360
```

```
actgacgaat atatcaacac tattctgcct ccgctgacta aagcactgtt taaatatgtt      420
cgtgaaggta aatatacttt ctgtactcct ggtcacatgg gcggtactgc attccagaaa      480
agcccggtag gtagcctgtt ctatgatttc tttggtccga ataccatgaa atctgatatt      540
tccatttcag tatctgaact gggttctctg ctggatcaca gtggtccaca caaagaagca      600
gaacagtata tcgctcgcgt ctttaacgca gaccgcagct acatggtgac caacggtact      660
tccactgcga acaaaattgt tggtatgtac tctgctccgg caggcagcac cattctgatt      720
gaccgtaact gccacaaatc gctgacccac ctgatgatga tgagcgatgt tacgccaatc      780
tatttccgcc cgaccgtaa cgcttacggt attcttggtg gtatcccaca gagtgaattc      840
cagcacgcta ccattgctaa gcgcgtgaaa gaaacaccaa acgcaacctg gccggtacat      900
gctgtaatta ccaactctac ctatgatggt ctgctgtaca caccgactt catcaagaaa      960 acactggatg tgaaatccat ccactttgac tccgcgtggg tgccttacac caacttctca     1020
ccgatttacg aaggtaaatg cggtatgagc ggtggccgtg tagaagggaa agtgatttac     1080
gaaacccagt ccactcacaa actgctggcg gcgttctctc aggcttccat gatccacgtt     1140
aaaggtgacg taaacgaaga aacctttaac gaagcctaca tgatgcacac caccacttct     1200
ccgcactacg gtatcgtggc gtccactgaa accgctgcgg cgatgatgaa gggtaatgct     1260
ggtaagcgtc tgatcaacgg ttccattgaa cgtgcgatca aattccgtaa agagatcaaa     1320
cgtctgagaa cggaatctga tggctggttc tttgatgttt ggcagccgga tcatatcgat     1380
acgactgaat gctggccgct gcgttctgac agcacctggc acggcttcaa aaacatcgat     1440
aacgagcaca tgtatcttga cccgatcaaa gtcaccctgc tgactccggg gatggaaaaa     1500
gacggcacca tgagcgactt tggtattccg gccagcatcg tggcgaaata cctcgacgaa     1560
catggcatcg ttgttgagaa aaccggtccg tataacctgc tgttcctgtt cagcatcggt     1620
atcgataaga ccaaagcact gagcctgctg cgtgctctga ctgacttcaa acgtgcgttc     1680
gacctgaacc tgcgtgtgaa aaacatgctg ccgtctctgt atcgtgaaga tcctgaattc     1740
tatgaaaaca tgcgtattca ggaactggct caaaatatcc acaaactgat tgttcaccac     1800
aatctgccgg atctgatgta tcgcgcattt gaagtgctgc cgacgatggt aatgactccg     1860
tatgctgcgt tccagaaaga gctgcacggt atgaccgaag aagtttacct cgacgaaatg     1920
gtaggtcgta ttaacgccaa tatgatcctt ccgtatccgc cgggagttcc tctggtaatg     1980
ccgggtgaaa tgatcaccga agaaagccgt ccggttctgg agttcctgca gatgctgtgt     2040
gaaatcggcg ctcactatcc gggctttgaa accgatattc acggtgcata ccgtcaggct     2100
gatggccgct ataccgttaa ggtattgaaa gaagaaagca aaaaataa                  2148
```

<210> SEQ ID NO 13
<211> LENGTH: 2148
<212> TYPE: DNA
<213> ORGANISM: Escherichia coli

<400> SEQUENCE: 13

```
atgaacgtta ttgcaatatt gaatcacatg ggggtttatt gtaaagaaga acccatccgt       60
gaacttcatc gcgcgcttga acgtctgaac ttccagattt tttacccgaa cgaccgtgac      120
gacttattat gtctgatcga aaacaatgcg cgtctgtgcg gcgttatttt tgactgggat      180
aaatataatc tcgagctgtg cgaagaaatt agcaaaatga acgagaacct gccgttgtac      240
gcgttcgcta atacgtattc cactctcgat gtaagcctga atgacctgcg tttacagatt      300
agcttctttg aatatgcgct gggtgctgct gaagatattg ctaataagat caagcagacc      360
```

```
actgacgaat atatcaacac tattctgcct ccgctgacta aagcactgtt taaatatgtt      420
cgtgaaggta aatatacttt ctgtactcct ggtcacatgg gcggtactgc attccagaaa      480
agcccggtag gtagcctgtt ctatgatttc tttggtccga ataccatgaa atctgatatt      540
tccatttcag tatctgaact gggttctctg ctggatcaca gtggtccaca caaagaagca      600
gaacagtata tcgctcgcgt cttttaacgca gaccgcagct acatggtgac caacggtact      660
tccactgcga acaaaattgt tggtatgtac tctgctccgg caggcagcac cattctgatt      720
gaccgtaact gccacaaatc gctgacccac ctgatgatga tgagcgatgt tacgccaatc      780
tatttccgcc cgaccgtaa cgcttacggt attcttggtg tatcccaca gagtgaattc       840
cagcacgcta ccattgctaa gcgcgtgaaa gaaacaccaa acgcaacctg ccggtacat       900
gctgtaatta ccaactctac ctatgatggt ctgctgtaca acccgactt catcaagaaa       960
acactggatg tgaaatccat ccactttgac tccgcgtggg tgccttacac caacttctca     1020
ccgatttacg aaggtaaatg cggtatgagc ggtggccgtg tagaagggaa agtgatttac     1080
gaaacccagt ccactcacaa actgctggcg gcgttctctc aggcttccat gatccacgtt     1140
aaaggtgaca taaacgaaga aacctttaac gaagcctaca tgatgcacac caccacttct     1200
ccgcactacg gtatcgtggc gtccactgaa accgctgcgg cgatgatgaa gggtaatgct     1260
ggtaagcgtc tgatcaacgg ttccattgaa cgtgcgatca aattccgtaa agagatcaaa     1320
cgtctgagaa cggaatctga tggctggttc tttgatgttt ggcagccgga tcatatcgat     1380
acgactgaat gctggccgct gcgttctgac agcacctggc acggcttcaa aaacatcgat     1440
aacgagcaca tgtatcttga cccgatcaaa gtcaccctgc tgactccggg gatggaaaaa     1500
gacggcacca tgagcgactt tggtattccg ccagcatcg tggcgaaata cctcgacgaa      1560
catggcatcg ttgttgagaa aaccggtccg tataacctgc tgttcctgtt cagcatcggt     1620
atcgataaga ccaaagcact gagcctgctg cgtgctctga ctgacttcaa acgtgcgttc     1680
gacctgaacc tgcgtgtgaa aaacatgctg ccgtctctgt atcgtgaaga tcctgaattc     1740
tatgaaaaca tgcgtattca ggaactggct caaaatatcc acaaactgat tgttcaccac     1800
aatctgccgg atctgatgta tcgcgcattt gaagtgctgc cgacgatggt aatgactccg     1860
tatgctgcgt tccagaaaga gctgcacggt atgaccgaag aagtttacct cgacgaaatg     1920
gtaggtcgta ttaacgccaa tatgatcctt ccgtatccgc cgggagttcc tctggtaatg     1980
ccgggtgaaa tgatcaccga agaaagccgt ccggttctgg agttcctgca gatgctgtgt     2040
gaaatcggcg ctcactatcc gggctttgaa accgatattc acggtgcata ccgtcaggct     2100
gatggccgct ataccgttaa ggtattgaaa gaagaaagca aaaaataa                   2148
```

<210> SEQ ID NO 14
<211> LENGTH: 2148
<212> TYPE: DNA
<213> ORGANISM: Escherichia coli

<400> SEQUENCE: 14

```
atgaacgtta ttgcaataat gggacacatg ggggtttatt gtaaagaaga acccatccgt       60
gaacttcatc gcgcgcttga acgtctgaac ttccagattt ttacccgaa cgaccgtgac       120
gacttattat gtctgatcga aaacaatgcg cgtctgtgcg gcgttatttt tgactgggat       180
aaatataatc tcgagctgtg cgaagaaatt agcaaaatga acgagaacct gccgttgtac       240
gcgttcgcta atacgtattc cactctcgat gtaagcctga atgacctgcg tttacagatt       300
```

```
agcttctttg aatatgcgct gggtgctgct gaagatattg ctaataagat caagcagacc    360
actgacgaat atatcaacac tattctgcct ccgctgacta aagcactgtt taaatatgtt    420
cgtgaaggta aatatacttt ctgtactcct ggtcacatgg gcggtactgc attccagaaa    480
agcccggtag gtagcctgtt ctatgatttc tttggtccga ataccatgaa atctgatatt    540
tccatttcag tatctgaact gggttctctg ctggatcaca gtggtccaca caagaagca    600
gaacagtata tcgctcgcgt ctttaacgca gaccgcagct acatggtgac caacggtact    660
tccactgcga acaaaattgt tggtatgtac tctgctccgg caggcagcac cattctgatt    720
gaccgtaact gccacaaatc gctgacccac ctgatgatga tgagcgatgt tacgccaatc    780
tatttccgcc cgaccgtaa cgcttacggt attcttggtg gtatcccaca gagtgaattc    840
cagcacgcta ccattgctaa cgcgtgaaa gaaacaccaa acgcaacctg ccggtacat    900
gctgtaatta ccaactctac ctatgatggt ctgctgtaca caccgactt catcaagaaa    960
acactggatg tgaaatccat ccactttgac tccgcgtggg tgccttacac caacttctca   1020
ccgatttacg aaggtaaatg cggtatgagc ggtggccgtg tagaagggaa agtgatttac   1080
gaaacccagt ccactcacaa actgctggcg gcgttctctc aggcttccat gatccacgtt   1140
aaaggtgacg taaacgaaga aacctttaac gaagcctaca tgatgcacac caccacttct   1200
ccgcactacg gtatcgtggc gtccactgaa accgctgcgg cgatgatgaa gggtaatgct   1260
ggtaagcgtc tgatcaacgg ttccattgaa cgtgcgatca aattccgtaa agagatcaaa   1320
cgtctgagaa cggaatctga tggctggttc tttgatgttt ggcagccgga tcatatcgat   1380
acgactgaat gctggccgct gcgttctgac agcacctggc acggcttcaa aaacatcgat   1440
aacgagcaca tgtatcttga cccgatcaaa gtcaccctgc tgactccggg gatggaaaaa   1500
gacggcacca tgagcgactt tggtattccg ccagcatcg tggcgaaata cctcgacgaa   1560
catggcatcg ttgttgagaa aaccggtccg tataacctgc tgttcctgtt cagcatcggt   1620
atcgataaga ccaaagcact gagcctgctg cgtgctctga ctgacttcaa acgtgcgttc   1680
gacctgaacc tgcgtgtgaa aaacatgctg ccgtctctgt atcgtgaaga tcctgaattc   1740
tatgaaaaca tgcgtattca ggaactggct caaaatatcc acaaactgat tgttcaccac   1800
aatctgccgg atctgatgta tcgcgcattt gaagtgctgc cgacgatggt aatgactccg   1860
tatgctgcgt tccagaaaga gctgcacggt atgaccgaag aagtttacct cgacgaaatg   1920
gtaggtcgta ttaacgccaa tatgatcctt ccgtatccgc cgggagttcc tctggtaatg   1980
ccgggtgaaa tgatcaccga agaaagccgt ccggttctgg agttcctgca gatgctgtgt   2040
gaaatcggcg ctcactatcc gggctttgaa accgatattc acggtgcata ccgtcaggct   2100
gatggccgct ataccgttaa ggtattgaaa gaagaaagca aaaaataa                2148
```

<210> SEQ ID NO 15
<211> LENGTH: 715
<212> TYPE: PRT
<213> ORGANISM: Escherichia coli

<400> SEQUENCE: 15

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

```
Asn Ala Arg Leu Cys Gly Val Ile Phe Asp Trp Asp Lys Tyr Asn Leu
 50              55                  60

Glu Leu Cys Glu Glu Ile Ser Lys Met Asn Glu Asn Leu Pro Leu Tyr
 65                  70                  75                  80

Ala Phe Ala Asn Thr Tyr Ser Thr Leu Asp Val Ser Leu Asn Asp Leu
                 85                  90                  95

Arg Leu Gln Ile Ser Phe Phe Glu Tyr Ala Leu Gly Ala Ala Glu Asp
                100                 105                 110

Ile Ala Asn Lys Ile Lys Gln Thr Thr Asp Glu Tyr Ile Asn Thr Ile
                115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
```

-continued

```
            465                 470                 475                 480
Asn Glu His Met Tyr Leu Asp Pro Ile Lys Val Thr Leu Leu Thr Pro
                    485                 490                 495
Gly Met Glu Lys Asp Gly Thr Met Ser Asp Phe Gly Ile Pro Ala Ser
                500                 505                 510
Ile Val Ala Lys Tyr Leu Asp Glu His Gly Ile Val Val Glu Lys Thr
                515                 520                 525
Gly Pro Tyr Asn Leu Leu Phe Leu Phe Ser Ile Gly Ile Asp Lys Thr
            530                 535                 540
Lys Ala Leu Ser Leu Leu Arg Ala Leu Thr Asp Phe Lys Arg Ala Phe
545                 550                 555                 560
Asp Leu Asn Leu Arg Val Lys Asn Met Leu Pro Ser Leu Tyr Arg Glu
                565                 570                 575
Asp Pro Glu Phe Tyr Glu Asn Met Arg Ile Gln Glu Leu Ala Gln Asn
                580                 585                 590
Ile His Lys Leu Ile Val His His Asn Leu Pro Asp Leu Met Tyr Arg
                595                 600                 605
Ala Phe Glu Val Leu Pro Thr Met Val Met Thr Pro Tyr Ala Ala Phe
            610                 615                 620
Gln Lys Glu Leu His Gly Met Thr Glu Glu Val Tyr Leu Asp Glu Met
625                 630                 635                 640
Val Gly Arg Ile Asn Ala Asn Met Ile Leu Pro Tyr Pro Pro Gly Val
                    645                 650                 655
Pro Leu Val Met Pro Gly Glu Met Ile Thr Glu Glu Ser Arg Pro Val
                    660                 665                 670
Leu Glu Phe Leu Gln Met Leu Cys Glu Ile Gly Ala His Tyr Pro Gly
                675                 680                 685
Phe Glu Thr Asp Ile His Gly Ala Tyr Arg Gln Ala Asp Gly Arg Tyr
                690                 695                 700
Thr Val Lys Val Leu Lys Glu Glu Ser Lys Lys
705                 710                 715
```